US008435734B2

(12) United States Patent
Kiyosawa et al.

(10) Patent No.: US 8,435,734 B2
(45) Date of Patent: May 7, 2013

(54) CANCER MARKER AND USE THEREOF

(75) Inventors: Hidenori Kiyosawa, Tsukuba (JP); Hiroshi Yasue, Tsukuba (JP); Nobuhiro Ohkohchi, Tsukuba (JP)

(73) Assignees: Riken, Wako-shi (JP); National Institute of Agrobiological Sciences, Tsukuba-shi (JP); University of Tsukuba, Tsukuba-shi (JP)

( * ) Notice: Subject to any disclaimer, the term of this patent is extended or adjusted under 35 U.S.C. 154(b) by 58 days.

(21) Appl. No.: 12/129,923

(22) Filed: May 30, 2008

(65) Prior Publication Data

US 2008/0299579 A1 Dec. 4, 2008

(30) Foreign Application Priority Data

May 31, 2007 (JP) ................................ 2007-146342

(51) Int. Cl.
*C12Q 1/68* (2006.01)

(52) U.S. Cl.
USPC .......................................................... 435/6.1

(58) Field of Classification Search .................... 435/6.1
See application file for complete search history.

(56) References Cited

U.S. PATENT DOCUMENTS 7,709,616 B2 * 5/2010 Bentwich et al. ............ 536/23.1
7,888,010 B2 * 2/2011 Brown et al. ................ 435/6.14
2003/0138432 A1 * 7/2003 Glazier ...................... 424/178.1
2003/0194406 A1 * 10/2003 Reinhard et al. ........... 424/155.1
2003/0194704 A1 * 10/2003 Penn et al. ........................ 435/6
2005/0009771 A1 * 1/2005 Levanon et al. ................ 514/44
2006/0134663 A1 * 6/2006 Harkin et al. ..................... 435/6

FOREIGN PATENT DOCUMENTS

WO WO 2005/098029 * 10/2005
WO 2005/118806 A2 12/2005

OTHER PUBLICATIONS

Khochbin et al. (The EMBO Journal 8, 4107-4114, 1989).*
Eccles et al. Oncogene 9: 2059-2063, 1994.*
Kiyosawa et al., *Genome Research*, 13: 1324-1334 (2003).
Kiyosawa et al., *Genome Research*, 15: 463-474 (2005).
Yelin et al., *Nature Biotechnology*, 21: 379-386 (2003).
Cai et al., *RNA*, 10: 1957-1966 (2004).
Lee at al., *Nature*, 425: 415-419 (2003).
Klimov et al., *Journal of Bioinformatics and Computational Biology*, 4(2): 515-521 (2006).
Thrash-Bingham et al., *Journal of the National Cancer Institute*, 91(2): 143-151 (1999).
Tommasi et al., *The Journal of Biological Chemistry*, 274(39): 27829-27838 (1999).

* cited by examiner

*Primary Examiner* — Brian Whiteman
(74) *Attorney, Agent, or Firm* — Leydig, Voit & Mayer, Ltd.

(57) ABSTRACT

This invention provides a method for cancer diagnosis comprising measuring an endogenous antisense RNA whose relative expression to a sense RNA changes cancer-specifically in RNA-containing samples collected from a mammal. Also provided are endogenous antisense RNAs useful as cancer markers, and cancer diagnostic reagents containing the same.

4 Claims, 54 Drawing Sheets

D
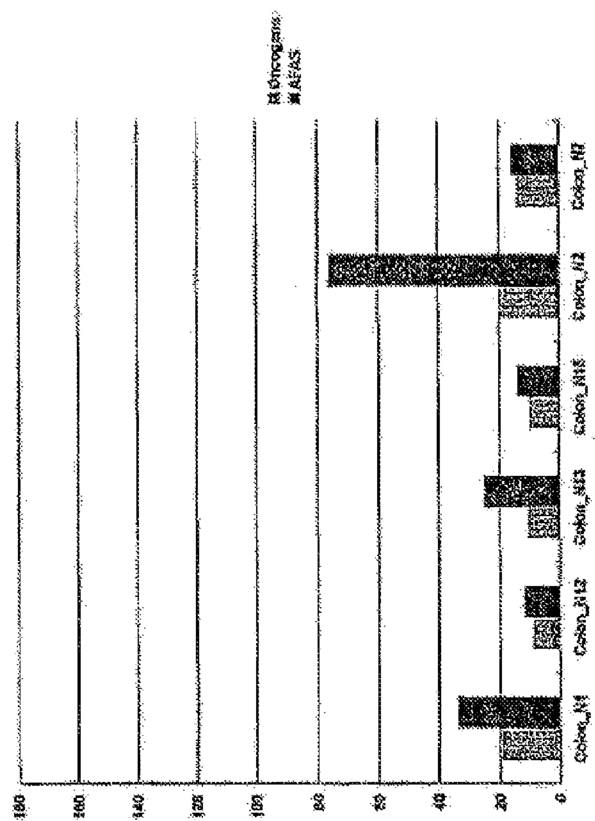
FIG. 6
C
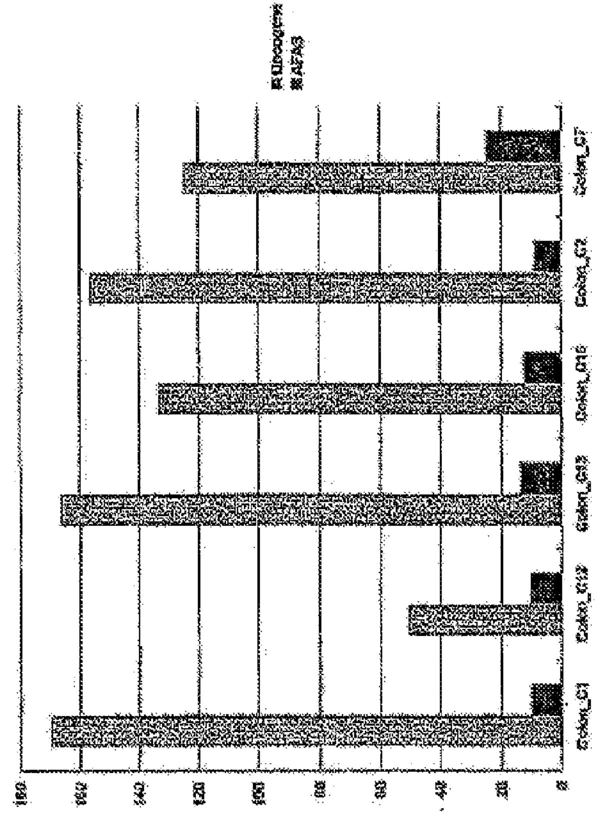

B
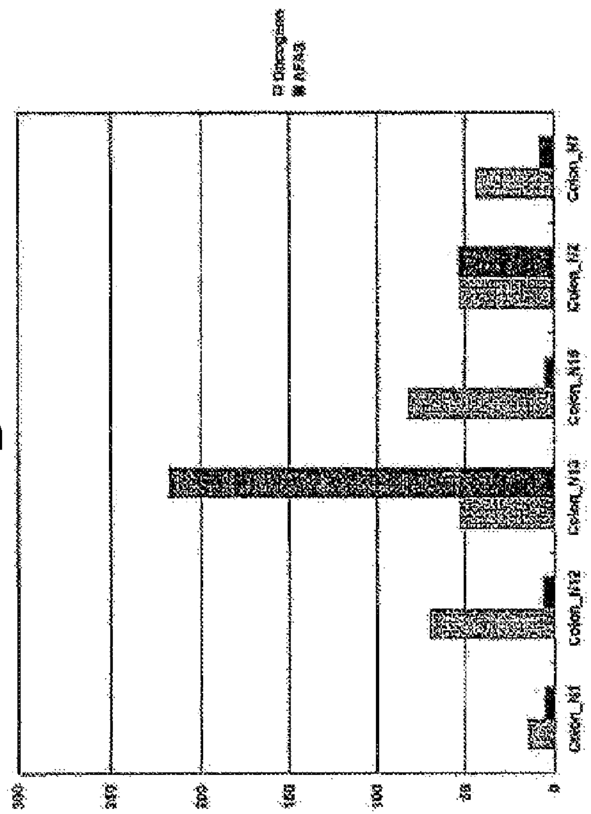
FIG. 9
A
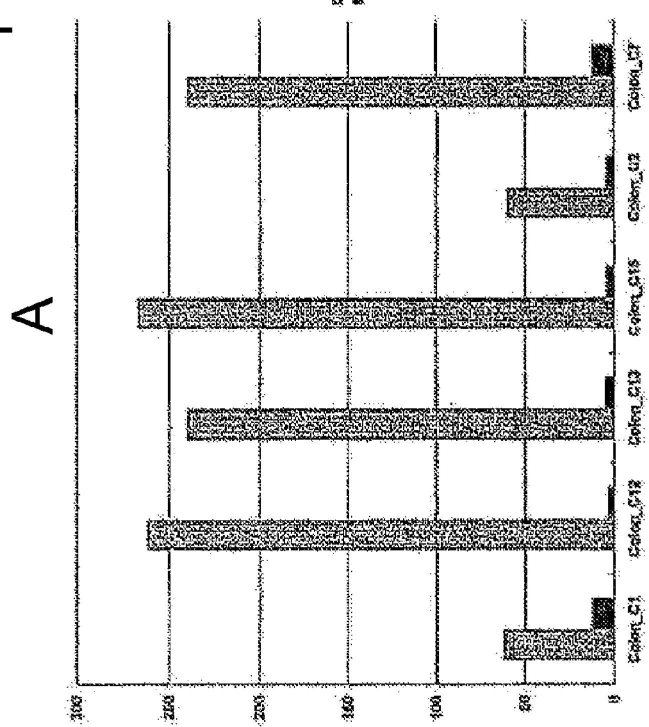

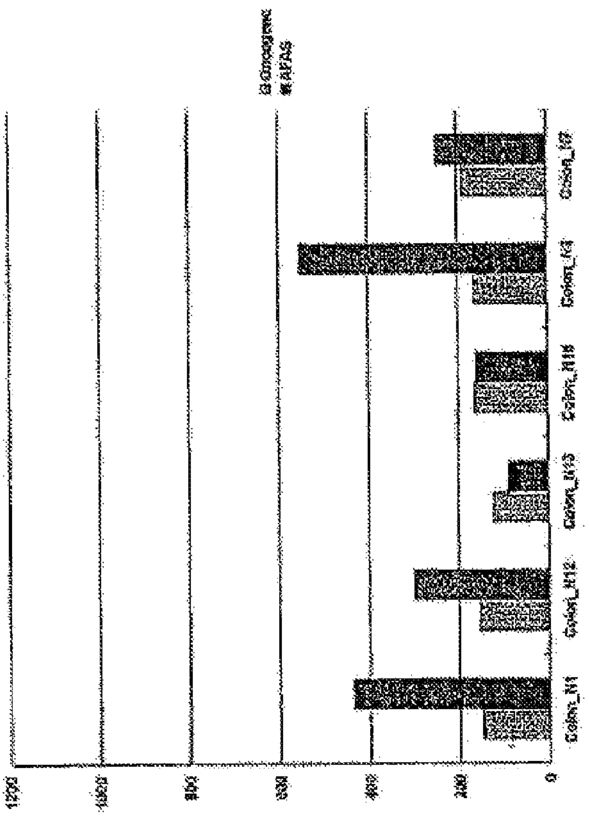
FIG. 12
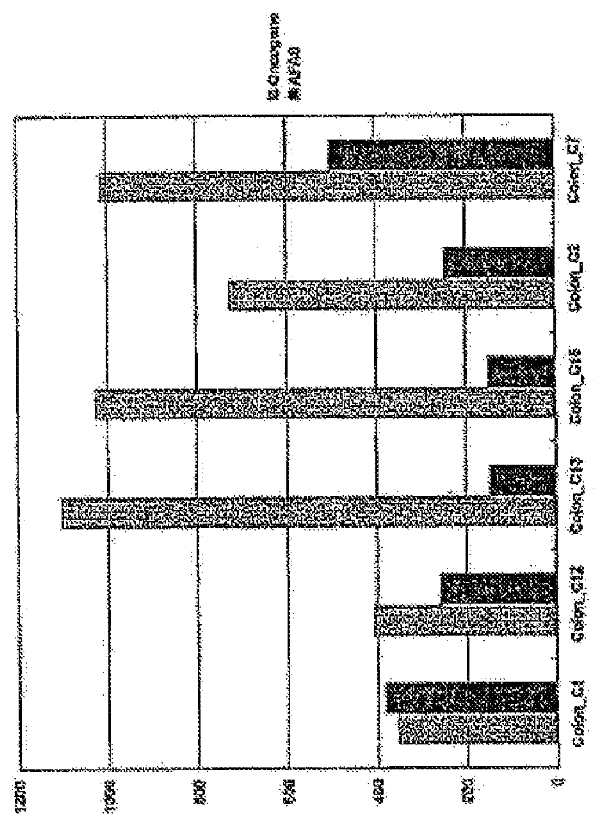

Figure 17:
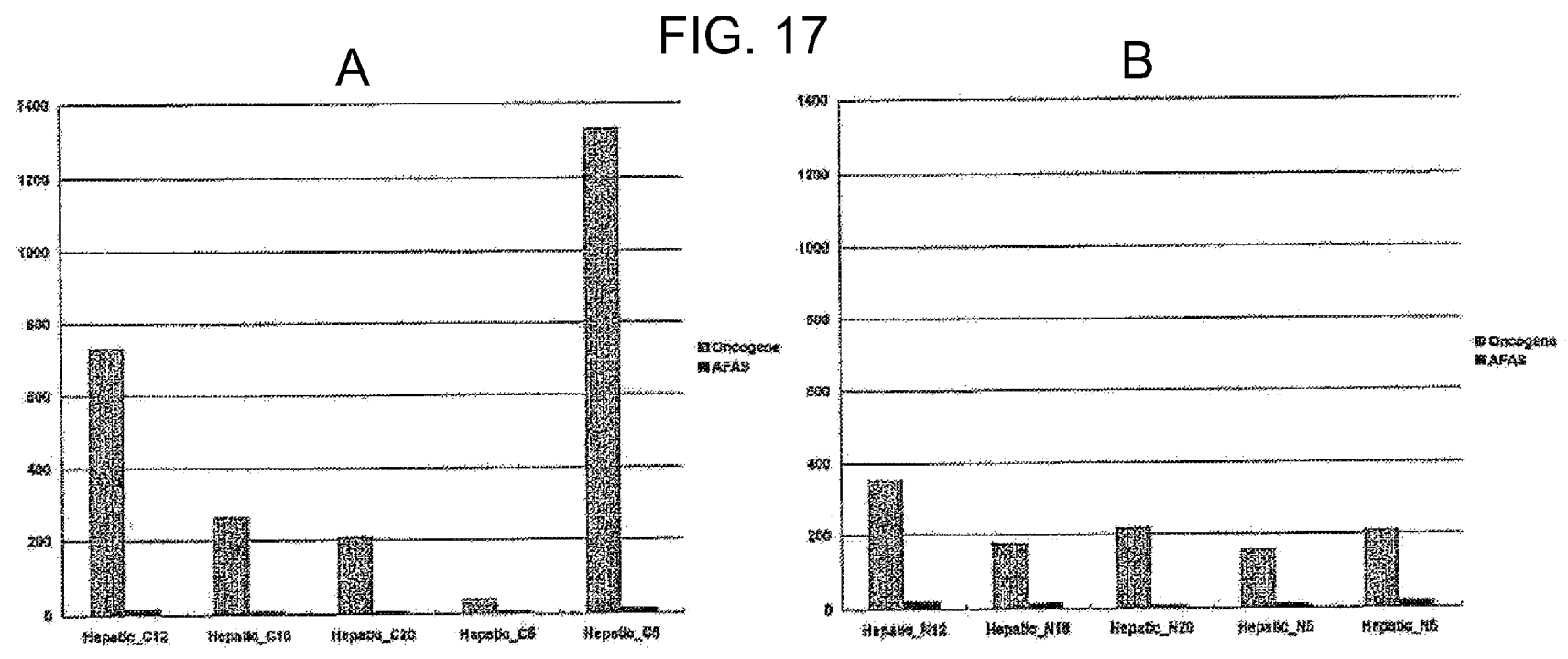

Hepatic_C12
Hepatic_C16
Hepatic_C20
Hepatic_C5
Hepatic_C6

Oncogene
AFAS

B 1400
1200
1000
800
600
400
200
0

Hepatic_N12
Hepatic_N16
Hepatic_N20
Hepatic_N5
Hepatic_N6

Oncogene
AFAS

SEQUENCE LISTING

```
<160> NUMBER OF SEQ ID NOS: 46

<210> SEQ ID NO 1
<211> LENGTH: 60
<212> TYPE: RNA
<213> ORGANISM: Homo sapiens

<400> SEQUENCE: 1

gaucacgggc cuuguacacu gucccauagg caccgacacc aauuucagcc acuggcucau     60


<210> SEQ ID NO 2
<211> LENGTH: 60
<212> TYPE: RNA
<213> ORGANISM: Homo sapiens

<400> SEQUENCE: 2
```

ucugccacuu gcacacuaua aaacugacug ucacauuuac ugucgcucau gaugcagcgu 60

<210> SEQ ID NO 3
<211> LENGTH: 60
<212> TYPE: RNA
<213> ORGANISM: Homo sapiens

<400> SEQUENCE: 3
uuuuggcauc aucacagacu ucagcuacug uggggua aau gaacggggca uugucauuca 60

<210> SEQ ID NO 4
<211> LENGTH: 60
<212> TYPE: RNA
<213> ORGANISM: Homo sapiens

<400> SEQUENCE: 4
acaccaacca gcugcagcau cuucuugggc acacaauuau ucugcaugaa ccgaucaaua 60

<210> SEQ ID NO 5
<211> LENGTH: 60
<212> TYPE: RNA
<213> ORGANISM: Homo sapiens

<400> SEQUENCE: 5
acugaggugg cagucgacca ccucaccugu cucucgaacc acugguucuu cuuuuucccg 60

<210> SEQ ID NO 6
<211> LENGTH: 60
<212> TYPE: RNA
<213> ORGANISM: Homo sapiens

<400> SEQUENCE: 6
ugaaacaagu uuucccucca guugggcuau uuucccuuga gacucuucga gacucccuuug 60

<210> SEQ ID NO 7
<211> LENGTH: 60
<212> TYPE: RNA
<213> ORGANISM: Homo sapiens

<400> SEQUENCE: 7
acugccgcug aauaaaacga acccagcaac uuccgaaaac agaaaauccg ccaaaggaaa 60

<210> SEQ ID NO 8
<211> LENGTH: 60
<212> TYPE: RNA
<213> ORGANISM: Homo sapiens

<400> SEQUENCE: 8
uuugaaguca ucugggcuga gacaggugug gaaacagacu uccuuuuggc cauacaaagu 60

<210> SEQ ID NO 9
<211> LENGTH: 60
<212> TYPE: RNA
<213> ORGANISM: Homo sapiens

<400> SEQUENCE: 9
uguucuucaa auuccuccug aauuuuagug aauaaggcuu cuagucucuu uuguugggcc 60

<210> SEQ ID NO 10
<211> LENGTH: 60
<212> TYPE: RNA
<213> ORGANISM: Homo sapiens

<400> SEQUENCE: 10
uuacaccaaa cuguaccagg aacuuaacga uuucugugug gccugcacac acagcauugu 60

<210> SEQ ID NO 11
<211> LENGTH: 60
<212> TYPE: RNA
<213> ORGANISM: Homo sapiens

<400> SEQUENCE: 11
ugcagaugag ccauccacca ggaagacuau gucucucuug uugacuucaa ugacuugugu 60

<210> SEQ ID NO 12
<211> LENGTH: 60
<212> TYPE: RNA
<213> ORGANISM: Homo sapiens

<400> SEQUENCE: 12
cagaaagcac gaaccucuuc ugucgguugc gggcacucag cccaucagau gggucgggca 60

<210> SEQ ID NO 13
<211> LENGTH: 60
<212> TYPE: RNA
<213> ORGANISM: Homo sapiens

<400> SEQUENCE: 13
acgacuuugg agggugggac aaacacaggu gccucauuca cauccuccac guggaccacu 60

<210> SEQ ID NO 14
<211> LENGTH: 60
<212> TYPE: RNA
<213> ORGANISM: Homo sapiens

<400> SEQUENCE: 14
acucccucgg aaggugUccu ggguaaacuu gggcuugugg ucauucuggu cggucacgau 60

<210> SEQ ID NO 15
<211> LENGTH: 60
<212> TYPE: RNA
<213> ORGANISM: Homo sapiens

<400> SEQUENCE: 15
uucuuuccug gacugucucg ccauuccgca cagugaaguc aucauuauca gugcuaaaca 60

<210> SEQ ID NO 16
<211> LENGTH: 60
<212> TYPE: RNA
<213> ORGANISM: Homo sapiens

<400> SEQUENCE: 16
ucacugagca cuaguccagc caaggggUca guggaggggc ccccagaggc cccagccccc 60

<210> SEQ ID NO 17
<211> LENGTH: 60
<212> TYPE: RNA
<213> ORGANISM: Homo sapiens

<400> SEQUENCE: 17
aucuucauca cauuguccuc agucaccagc acauugcggg cagccagguc ccgguggaua 60

<210> SEQ ID NO 18
<211> LENGTH: 60
<212> TYPE: RNA
<213> ORGANISM: Homo sapiens

<400> SEQUENCE: 18
uagaagcggc ugcuugacug guaaccaaag acgaagccag cauagucguc gucccgguca 60

<210> SEQ ID NO 19
<211> LENGTH: 60
<212> TYPE: RNA
<213> ORGANISM: Homo sapiens

<400> SEQUENCE: 19
uuugacaaca gaaagcaucc cuucguuggu uugaggguug guguggauuu caaagcucug 60

<210> SEQ ID NO 20
<211> LENGTH: 60
<212> TYPE: RNA
<213> ORGANISM: Homo sapiens

<400> SEQUENCE: 20
aggaucgaug uagaacaugu ugggagaugg cuugucaggc gucuguugac ggauauuaua 60

<210> SEQ ID NO 21
<211> LENGTH: 60
<212> TYPE: RNA
<213> ORGANISM: Homo sapiens

<400> SEQUENCE: 21
auaucuucau ugccggcgca uuuuaguauu uuggacauac uggugagguu cacgcccaug 60

<210> SEQ ID NO 22
<211> LENGTH: 60
<212> TYPE: RNA
<213> ORGANISM: Homo sapiens

<400> SEQUENCE: 22
aaucuuccca gggagggauu cggucucccc accugucagc cagggagaga auccuagauu 60

<210> SEQ ID NO 23
<211> LENGTH: 60
<212> TYPE: RNA
<213> ORGANISM: Homo sapiens

<400> SEQUENCE: 23
uguugaucuu cgccuuauuu ucagcauuaa uuuucgaguu ccuggugacu cggagcgcca 60

<210> SEQ ID NO 24
<211> LENGTH: 60
<212> TYPE: RNA
<213> ORGANISM: Homo sapiens

<400> SEQUENCE: 24
acagcugagu ugcccagcac cagacagcgu uuucugacag ugcaugcagc agucacacca 60

<210> SEQ ID NO 25
<211> LENGTH: 60
<212> TYPE: RNA
<213> ORGANISM: Homo sapiens

<400> SEQUENCE: 25
uuugauuucu gccuugaugu cacuuaggau aggagaagau gauguauagg guuuaguggg 60

<210> SEQ ID NO 26
<211> LENGTH: 60
<212> TYPE: RNA
<213> ORGANISM: Homo sapiens

<400> SEQUENCE: 26
ugaagaaacc acacuuccau aguauaaaca cuaauaaagc aagcaucaag aucccagcga 60

<210> SEQ ID NO 27
<211> LENGTH: 60
<212> TYPE: RNA
<213> ORGANISM: Homo sapiens

<400> SEQUENCE: 27
uauuuaaaug ccaaauaauc uuccagguag ugcugcuucu gaaguuaucu cuuaauccuc 60

<210> SEQ ID NO 28
<211> LENGTH: 60
<212> TYPE: RNA
<213> ORGANISM: Homo sapiens

<400> SEQUENCE: 28
ucugugagaa cuccugacgu cugaagcuug acucccaagu uuccauagca acaggaaaaa 60

<210> SEQ ID NO 29
<211> LENGTH: 60
<212> TYPE: RNA
<213> ORGANISM: Homo sapiens

<400> SEQUENCE: 29
cucuacacua aggguaugu ucccucuugu cccuuucccu accuuuauau uuggggguccu 60

<210> SEQ ID NO 30
<211> LENGTH: 60
<212> TYPE: RNA
<213> ORGANISM: Homo sapiens

<400> SEQUENCE: 30
guucaagauu uagccaaggc uguggcaaag guguaacuug uaaacuugag uuggaguacu 60

<210> SEQ ID NO 31
<211> LENGTH: 60
<212> TYPE: RNA
<213> ORGANISM: Homo sapiens

<400> SEQUENCE: 31
ccccaccaua ugaauuguac agaauauuuc uauugaauuc ggaacugucc uuuccuuggc 60

<210> SEQ ID NO 32
<211> LENGTH: 60
<212> TYPE: RNA
<213> ORGANISM: Homo sapiens

<400> SEQUENCE: 32
auccuuucua cuuguccagu ucaaauaaga aauaaggaca agccuaacuu cauaguaacc 60

<210> SEQ ID NO 33
<211> LENGTH: 60
<212> TYPE: RNA
<213> ORGANISM: Homo sapiens

<400> SEQUENCE: 33
guaccacaua cacuucugug gacuuuuagc auuugugggu agacuuaaug gccuucgugg 60

<210> SEQ ID NO 34
<211> LENGTH: 60
<212> TYPE: RNA
<213> ORGANISM: Homo sapiens

<400> SEQUENCE: 34
caaaaaucgu uuugcccgau uccguauugg uauacuuuug cuucaguugc auaucuuaaa 60

<210> SEQ ID NO 35
<211> LENGTH: 60
<212> TYPE: RNA
<213> ORGANISM: Homo sapiens

<400> SEQUENCE: 35
guaucucaga aauuagaaac uugcuacaga cuuacccgua auauuuguca agaucauagc 60

<210> SEQ ID NO 36
<211> LENGTH: 60
<212> TYPE: RNA
<213> ORGANISM: Homo sapiens

<400> SEQUENCE: 36
cuuuuucuga agccucuaac aaaugaucua guucagaagg aagcaaaauc ccuuaaucua 60

<210> SEQ ID NO 37
<211> LENGTH: 60
<212> TYPE: RNA
<213> ORGANISM: Homo sapiens

<400> SEQUENCE: 37
caggccggau ccuccugaag cccuuuucgc agcacugcua uccuccaaag ccauuguaaa 60

<210> SEQ ID NO 38
<211> LENGTH: 60
<212> TYPE: RNA
<213> ORGANISM: Homo sapiens

<400> SEQUENCE: 38
uuucccuguu gcguugcuau agaugaaggg ugaggacaau cguguauaug uacuagaacu 60

<210> SEQ ID NO 39
<211> LENGTH: 60
<212> TYPE: RNA
<213> ORGANISM: Homo sapiens

<400> SEQUENCE: 39
agcgucuuga cgggagcauu ggccccugag cccagagaag cuggaagccu gccgaaaaca 60

<210> SEQ ID NO 40
<211> LENGTH: 60
<212> TYPE: RNA
<213> ORGANISM: Homo sapiens

<400> SEQUENCE: 40
gacuguaaau auuuauuuau guguucacau ggucaaaauu ucaccacuga aacccugcac 60

<210> SEQ ID NO 41
<211> LENGTH: 60
<212> TYPE: RNA
<213> ORGANISM: Homo sapiens

<400> SEQUENCE: 41
ccaaagucug aucuggucua guuaaccuag aaguauuuuu gucucuuaga aauacuugug 60

<210> SEQ ID NO 42
<211> LENGTH: 60
<212> TYPE: RNA
<213> ORGANISM: Homo sapiens

<400> SEQUENCE: 42

```
gguuuacaaa uauuuuuagg acucacguua acucacauuu auacagcaga aaugcuauuu     60


<210> SEQ ID NO 43
<211> LENGTH: 60
<212> TYPE: RNA
<213> ORGANISM: Homo sapiens

<400> SEQUENCE: 43

aagaugcauc aagggcuugg cugugccuuc auaggucauc uaggguuuua uaaaggagga     60


<210> SEQ ID NO 44
<211> LENGTH: 60
<212> TYPE: RNA
<213> ORGANISM: Homo sapiens

<400> SEQUENCE: 44

uuuccagagg gguugagcag ggauccuggu uucaaugacg guuggaaaua gaaauuucca     60


<210> SEQ ID NO 45
<211> LENGTH: 60
<212> TYPE: RNA
<213> ORGANISM: Homo sapiens

<400> SEQUENCE: 45

ggcucggcuu ggauuauucu gcagguucau cucagaccca ccuuucagcc uuaagcagcc     60


<210> SEQ ID NO 46
<211> LENGTH: 60
<212> TYPE: RNA
<213> ORGANISM: Homo sapiens

<400> SEQUENCE: 46

agacuuaugg uuguuaaaaa ugucaucuca agucaaguca cuggucuguu ugcauuugau     60
```

CANCER MARKER AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 6,973 bytes ASCII (Text) file named "703094SequenceListing.txt," created May 29, 2008.

TECHNICAL FIELD OF THE INVENTION

The present invention relates to an endogenous antisense RNA with cancer-specific variation in expression level, a diagnostic method of cancer using same as a marker, a reagent therefor and the like.

BACKGROUND OF THE INVENTION

Antisense RNA is an RNA having a nucleotide sequence complementary to mRNA. Specifically, it is an RNA read from an opposite strand of a DNA strand encoding a sense gene. Sense-antisense RNAs are capable of forming a double-strand and, for example, it is known that a double-stranded RNA is necessary for RNA interference, a double-stranded RNA is involved in the regulation of translation of a protein by a small RNA called microRNA and the like.

About 2,500 pairs of sense-antisense genes have been identified in mouse, which include many noncoding genes that do not encode proteins (non-patent reference 1). About half of the sense-antisense gene pairs is considered to be coding-noncoding gene pairs. Also in human, the presence of about 2,600 pairs of sense-antisense RNA pairs is suggested (non-patent reference 2). However, experimental verification relating to the structures and expressions thereof is limited.

One of the present inventors and their coworkers have so far developed an oligo DNA chip that distinguishes and analyzes 1947 pairs of sense gene and antisense gene identified in mouse, and comprehensively analyzed the expression of sense-antisense genes (non-patent reference 3). As a result, they have found that more than 90% of the sense-antisense genes are expressed in actual tissues, and that the expression thereof shows tissue specificity. It has also been found that various sizes of RNAs are transcribed from the sense-antisense gene locus, most of the RNAs lack the poly(A) chain and they tend to be accumulated in the nucleus. Furthermore, RNA without the poly(A) chain was also found by analysis of Arabidopsis, and such properties were found to be common to animals and plants.

Nevertheless, the physiological role of such noncoding antisense RNAs has not been elucidated at all.

Meanwhile, some carcinomas have been reported to involve genes whose expression changes cancer-specifically (cancer marker genes). However, no reports are available that the expression of endogenous antisense RNAs, particularly of noncoding ones, changes specifically in cancers or other diseases.

non-patent reference 1: Kiyosawa et al, Genome Res. 13: 1324-1334 (2003)

non-patent reference 2: Yelin et al, Nat. Biotechnol. 21: 379-386 (2003)

non-patent reference 3: Kiyosawa et al, Genome Research, 15: 463-474 (2005)

DISCLOSURE OF THE INVENTION

Problems to be Solved by the Invention

The present invention is directed to the elucidation of the physiological functions of endogenous antisense RNAs, particularly of noncoding ones, and the provision of new uses of antisense RNAs, based on the physiological functions thereof elucidated. It is another object of the present invention to identify novel cancer marker genes and provide a more accurate method of cancer diagnosis.

Means of Solving the Problems

The present inventors artificially postulated, as a putative antisense RNA, an antisense strand sequence deduced from a known cDNA sequence, designed a probe for the antisense strand sequence (Artificial Antisense Sequence: AFAS) under the same conditions as for designing a probe for general cDNA sequences, i.e., conditions optimal for hybridization, and constructed a microarray containing the probe (AFAS probe) along with a probe for cDNA sequence (sense strand sequence). Furthermore, the present inventors labeled samples from cancer patients by random priming and, using the microarray, comprehensively analyzed the expression of sense-antisense gene pairs in each sample. As a result, they have found that, in 20 genes known as cancer genes, the balance of expression of sense strands and antisense strands is reversed between cancer tissues and the surrounding normal tissues. These results first demonstrated clearly that the expression of these cancer genes is regulated by antisense RNA and abnormality in the regulatory mechanism is closely related to cancer, and that endogenous antisense RNA has a physiological function to regulate the expression of a gene encoded by the corresponding sense strand.

The present inventors have conducted further studies based on these findings and found that an antisense RNA of the above-mentioned cancer gene is useful as a cancer marker, which resulted in the completion of the present invention.

Accordingly, the present invention provides the following.

[1] A method for cancer diagnosis, comprising measuring an endogenous antisense RNA in an RNA-containing sample collected from a mammal, which shows cancer-specifically varying relative expression to the corresponding sense RNA.

[2] The method of the above-mentioned [1], further comprising measurement of the sense RNA.

[3] The method of the above-mentioned [1] or [2] for diagnosis of colorectal cancer, wherein the endogenous antisense RNA is selected from the following (C1) to (C15):

(C1) an endogenous antisense RNA of mammalian CDK4 gene comprising a nucleotide sequence the same or substantially the same as the nucleotide sequence of SEQ ID NO:1, (C2) an endogenous antisense RNA of mammalian MAPK9 gene comprising a nucleotide sequence the same or substantially the same as the nucleotide sequence of SEQ ID NO:2, (C3) an endogenous antisense RNA of mammalian cadherin 13 gene comprising a nucleotide sequence the same or substantially the same as the nucleotide sequence of SEQ ID NO:3, (C4) an endogenous antisense RNA of mammalian cyclin B1 gene comprising a nucleotide sequence the same or substantially the same as the nucleotide sequence of SEQ ID NO:4, (C5) an endogenous antisense RNA of mammalian pLK gene comprising a nucleotide sequence the same or substantially the same as the nucleotide sequence of SEQ ID NO:5, (C6) an endogenous antisense RNA of mammalian RHAMM gene comprising a nucleotide sequence the same or substantially the same as the nucleotide sequence of SEQ ID NO:6, (C7) an endogenous antisense RNA of mammalian β3-endonexin gene comprising a nucleotide sequence the same or substantially the same as the nucleotide sequence of SEQ ID NO:7, (C8) an endogenous antisense RNA of mammalian BRCA2 gene comprising a nucleotide sequence the same or substantially the same as the nucleotide sequence of SEQ ID NO:8, (C9) an endogenous antisense RNA of mammalian BRCA2 gene comprising a nucleotide sequence the same or substantially the same as the nucleotide sequence of SEQ ID NO:9, (C10) an endogenous antisense RNA of mammalian BBP/53BP2 gene comprising a nucleotide sequence the same or substantially the same as the nucleotide sequence of SEQ ID NO:10, (C1) an endogenous antisense RNA of mammalian type IV collagen α3 gene comprising a nucleotide sequence the same or substantially the same as the nucleotide sequence of SEQ ID NO:11, (C12) an endogenous antisense RNA of mammalian MMP11 gene comprising a nucleotide sequence the same or substantially the same as the nucleotide sequence of SEQ ID NO:12, (C13) an endogenous antisense RNA of mammalian P-cadherin gene comprising a nucleotide sequence the same or substantially the same as the nucleotide sequence of SEQ ID NO:13, (C14) an endogenous antisense RNA of mammalian P-cadherin gene comprising a nucleotide sequence the same or substantially the same as the nucleotide sequence of SEQ ID NO:14, (C15) an endogenous antisense RNA of mammalian P-cadherin gene comprising a nucleotide sequence the same or substantially the same as the nucleotide sequence of SEQ ID NO:15.

[4] The method of the above-mentioned [1] or [2] for diagnosis of hepatic cancer, wherein the endogenous antisense RNA is selected from the following (H1) to (H12):

(H1) an endogenous antisense RNA of mammalian MAPK7 gene comprising a nucleotide sequence the same or substantially the same as the nucleotide sequence of SEQ ID NO:16, (H2) an endogenous antisense RNA of mammalian FGFR4 gene comprising a nucleotide sequence the same or substantially the same as the nucleotide sequence of SEQ ID NO:17, (H3) an endogenous antisense RNA of mammalian thrombospondin 2 gene comprising a nucleotide sequence the same or substantially the same as the nucleotide sequence of SEQ ID NO:18, (H4) an endogenous antisense RNA of mammalian cadherin 13 gene comprising a nucleotide sequence the same or substantially the same as the nucleotide sequence of SEQ ID NO:3, (H5) an endogenous antisense RNA of mammalian cadherin 13 gene comprising a nucleotide sequence the same or substantially the same as the nucleotide sequence of SEQ ID NO:19, (H6) an endogenous antisense RNA of mammalian cadherin 13 gene comprising a nucleotide sequence the same or substantially the same as the nucleotide sequence of SEQ ID NO:20, (H7) an endogenous antisense RNA of mammalian PCNA gene comprising a nucleotide sequence the same or substantially the same as the nucleotide sequence of SEQ ID NO:21, (H8) an endogenous antisense RNA of mammalian PDGFR gene comprising a nucleotide sequence the same or substantially the same as the nucleotide sequence of SEQ ID NO:22, (H9) an endogenous antisense RNA of mammalian cyclin B1 gene comprising a nucleotide sequence the same or substantially the same as the nucleotide sequence of SEQ ID NO:23, (H10) an endogenous antisense RNA of mammalian ERCC3 gene comprising a nucleotide sequence the same or substantially the same as the nucleotide sequence of SEQ ID NO:24, (H11) an endogenous antisense RNA of mammalian CD34 antigen gene comprising a nucleotide sequence the same or substantially the same as the nucleotide sequence of SEQ ID NO:25, (H12) an endogenous antisense RNA of mammalian integrin α6 gene comprising a nucleotide sequence the same or substantially the same as the nucleotide sequence of SEQ ID NO:26.

[5] An isolated endogenous antisense RNA selected from the following (C1) to (C15):

(C1) an endogenous antisense RNA of mammalian CDK4 gene comprising a nucleotide sequence the same or substantially the same as the nucleotide sequence of SEQ ID NO:1, (C2) an endogenous antisense RNA of mammalian MAPK9 gene comprising a nucleotide sequence the same or substantially the same as the nucleotide sequence of SEQ ID NO:2, (C3) an endogenous antisense RNA of mammalian cadherin 13 gene comprising a nucleotide sequence the same or substantially the same as the nucleotide sequence of SEQ ID NO:3, (C4) an endogenous antisense RNA of mammalian cyclin B1 gene comprising a nucleotide sequence the same or substantially the same as the nucleotide sequence of SEQ ID NO:4, (C5) an endogenous antisense RNA of mammalian pLK gene comprising a nucleotide sequence the same or substantially the same as the nucleotide sequence of SEQ ID NO:5, (C6) an endogenous antisense RNA of mammalian RHAMM gene comprising a nucleotide sequence the same or substantially the same as the nucleotide sequence of SEQ ID NO:6, (C7) an endogenous antisense RNA of mammalian β3-endonexin gene comprising a nucleotide sequence the same or substantially the same as the nucleotide sequence of SEQ ID NO:7, (C8) an endogenous antisense RNA of mammalian BRCA2 gene comprising a nucleotide sequence the same or substantially the same as the nucleotide sequence of SEQ ID NO:8, (C9) an endogenous antisense RNA of mammalian BRCA2 gene comprising a nucleotide sequence the same or substantially the same as the nucleotide sequence of SEQ ID NO:9, (C10) an endogenous antisense RNA of mammalian BBP/53BP2 gene comprising a nucleotide sequence the same or substantially the same as the nucleotide sequence of SEQ ID NO:10, (C11) an endogenous antisense RNA of mammalian type IV collagen α3 gene comprising a nucleotide sequence the same or substantially the same as the nucleotide sequence of SEQ ID NO:11, (C12) an endogenous antisense RNA of mammalian MMP11 gene comprising a nucleotide sequence the same or substantially the same as the nucleotide sequence of SEQ ID NO:12, (C13) an endogenous antisense RNA of mammalian P-cadherin gene comprising a nucleotide sequence the same or substantially the same as the nucleotide sequence of SEQ ID NO:13, (C14) an endogenous antisense RNA of mammalian P-cadherin gene comprising a nucleotide sequence the same or substantially the same as the nucleotide sequence of SEQ ID NO:14, (C15) an endogenous antisense RNA of mammalian P-cadherin gene comprising a nucleotide sequence the same or substantially the same as the nucleotide sequence of SEQ ID NO:15, which is a colorectal cancer marker for mammals.

[6] An isolated endogenous antisense RNA selected from the following (H1) to (H12)

(H1) an endogenous antisense RNA of mammalian MAPK7 gene comprising a nucleotide sequence the same or substantially the same as the nucleotide sequence of SEQ ID NO:16, (H2) an endogenous antisense RNA of mammalian FGFR4 gene comprising a nucleotide sequence the same or substantially the same as the nucleotide sequence of SEQ ID NO:17, (H3) an endogenous antisense RNA of mammalian thrombospondin 2 gene comprising a nucleotide sequence the same or substantially the same as the nucleotide sequence of SEQ ID NO:18, (H4) an endogenous antisense RNA of mammalian cadherin 13 gene comprising a nucleotide sequence the same or substantially the same as the nucleotide sequence of SEQ ID NO:3, (H5) an endogenous antisense RNA of mammalian cadherin 13 gene comprising a nucleotide sequence the same or substantially the same as the nucleotide sequence of SEQ ID NO:19, (H6) an endogenous antisense RNA of mammalian cadherin 13 gene comprising a nucleotide sequence the same or substantially the same as the nucleotide sequence of SEQ ID NO:20, (H7) an endogenous antisense RNA of mammalian PCNA gene comprising a nucleotide sequence the same or substantially the same as the nucleotide sequence of SEQ ID NO:21, (H8) an endogenous antisense RNA of mammalian PDGFR gene comprising a nucleotide sequence the same or substantially the same as the nucleotide sequence of SEQ ID NO:22, (H9) an endogenous antisense RNA of mammalian cyclin B1 gene comprising a nucleotide sequence the same or substantially the same as the nucleotide sequence of SEQ ID NO:23, (H10) an endogenous antisense RNA of mammalian ERCC3 gene comprising a nucleotide sequence the same or substantially the same as the nucleotide sequence of SEQ ID NO:24, (H11) an endogenous antisense RNA of mammalian CD34 antigen gene comprising a nucleotide sequence the same or substantially the same as the nucleotide sequence of SEQ ID NO:25, (H12) an endogenous antisense RNA of mammalian integrin α6 gene comprising a nucleotide sequence the same or substantially the same as the nucleotide sequence of SEQ ID NO:26, which is a hepatic cancer marker for mammals.

[7] A diagnostic agent of colorectal cancer comprising a nucleic acid comprising a nucleotide sequence hybridizable to the endogenous antisense RNA of the above-mentioned [5].

[8] A diagnostic agent of hepatic cancer comprising a nucleic acid comprising a nucleotide sequence hybridizable to the endogenous antisense RNA of the above-mentioned [6].

EFFECT OF THE INVENTION

Because an endogenous antisense RNA according to the present invention exhibits remarkably decreased absolute expression, or at least remarkably decreased relative expression to a sense RNA, in cancer patients, compared with healthy persons, cancers can be diagnosed efficiently by measuring the expression level of the antisense RNA, and, if necessary, also measuring the expression level of the corresponding sense RNA.

BRIEF DESCRIPTION OF THE DRAWINGS

Figure 17:
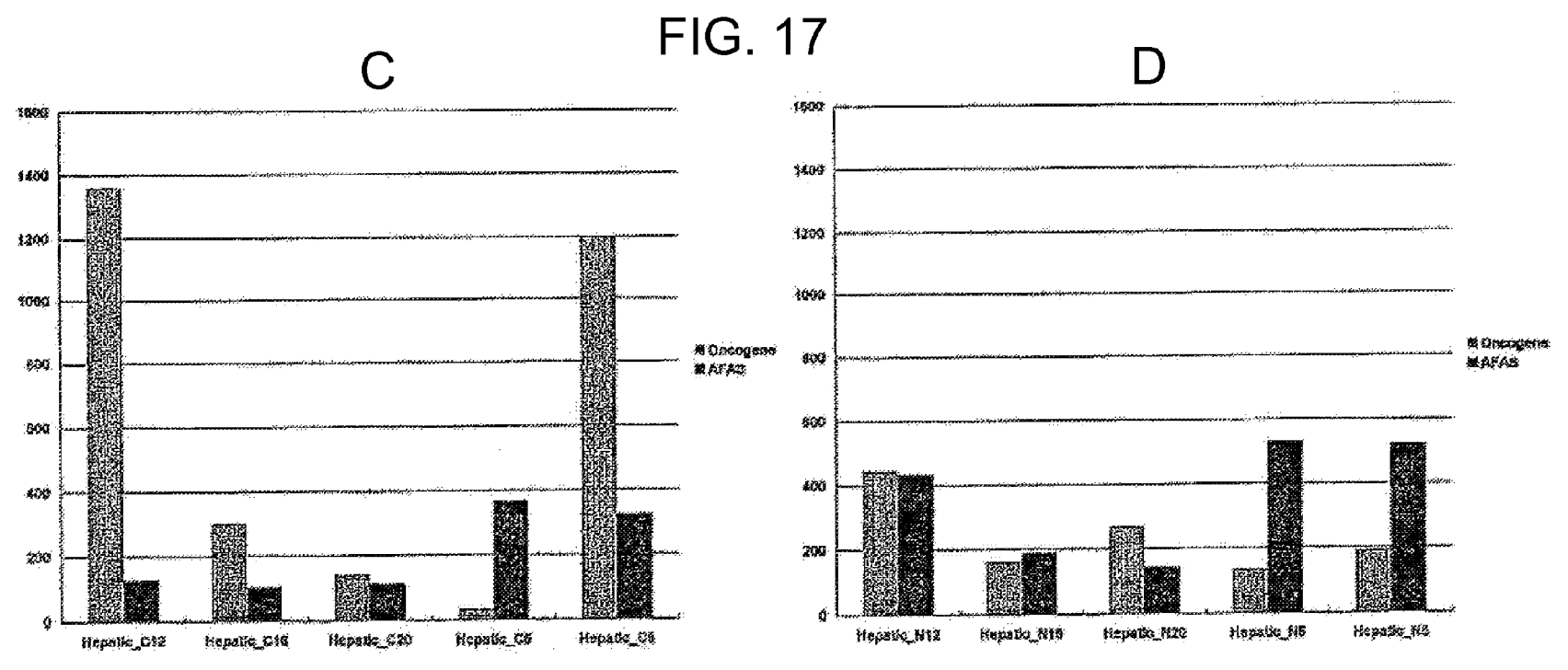

FIG. 17 shows the expression of FGFR4 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.

BEST MODE FOR CARRYING OUT THE INVENTION

Figure 1:
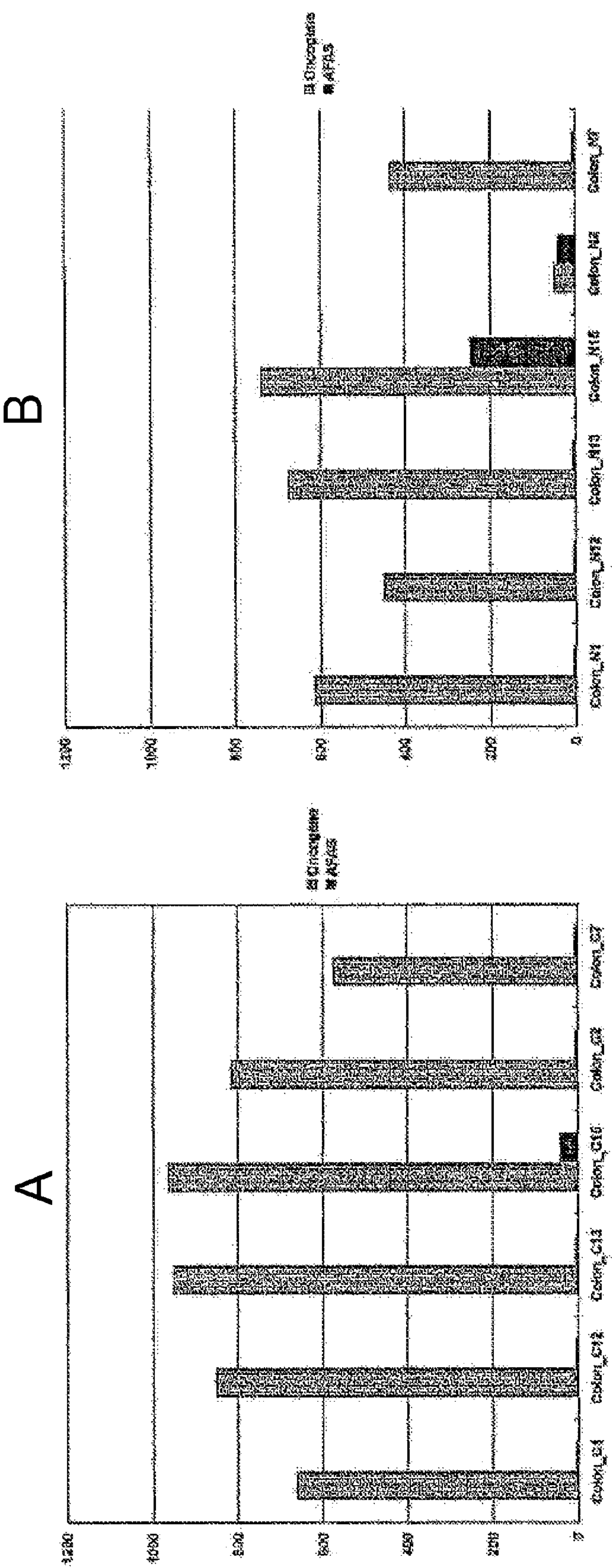
FIG. 1 shows the expression of CDK4 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.

An endogenous antisense RNA to be the cancer marker of the present invention is selected from the following (C1) to (C15) and (H1) to (H12):

(C1) an endogenous antisense RNA of mammalian CDK4 gene comprising a nucleotide sequence the same or substantially the same as the nucleotide sequence of SEQ ID NO:1, (C2) an endogenous antisense RNA of mammalian MAPK9 gene comprising a nucleotide sequence the same or substantially the same as the nucleotide sequence of SEQ ID NO:2, (C3) an endogenous antisense RNA of mammalian cadherin 13 gene comprising a nucleotide sequence the same or substantially the same as the nucleotide sequence of SEQ ID NO:3, (C4) an endogenous antisense RNA of mammalian cyclin B1 gene comprising a nucleotide sequence the same or substantially the same as the nucleotide sequence of SEQ ID NO:4, (C5) an endogenous antisense RNA of mammalian pLK gene comprising a nucleotide sequence the same or substantially the same as the nucleotide sequence of SEQ ID NO:5, (C6) an endogenous antisense RNA of mammalian RHAMM gene comprising a nucleotide sequence the same or substantially the same as the nucleotide sequence of SEQ ID NO:6, (C7) an endogenous antisense RNA of mammalian β3-endonexin gene comprising a nucleotide sequence the same or substantially the same as the nucleotide sequence of SEQ ID NO:7, (C8) an endogenous antisense RNA of mammalian BRCA2 gene comprising a nucleotide sequence the same or substantially the same as the nucleotide sequence of SEQ ID NO:8, (C9) an endogenous antisense RNA of mammalian BRCA2 gene comprising a nucleotide sequence the same or substantially the same as the nucleotide sequence of SEQ ID NO:9, (C10) an endogenous antisense RNA of mammalian BBP/53BP2 gene comprising a nucleotide sequence the same or substantially the same as the nucleotide sequence of SEQ ID NO:10, (C11) an endogenous antisense RNA of mammalian type IV collagen α3 gene comprising a nucleotide sequence the same or substantially the same as the nucleotide sequence of SEQ ID NO:11, (C12) an endogenous antisense RNA of mammalian MMP11 gene comprising a nucleotide sequence the same or substantially the same as the nucleotide sequence of SEQ ID NO:12, (C13) an endogenous antisense RNA of mammalian P-cadherin gene comprising a nucleotide sequence the same or substantially the same as the nucleotide sequence of SEQ ID NO:13, (C14) an endogenous antisense RNA of mammalian P-cadherin gene comprising a nucleotide sequence the same or substantially the same as the nucleotide sequence of SEQ ID NO:14, (C15) an endogenous antisense RNA of mammalian P-cadherin gene comprising a nucleotide sequence the same or substantially the same as the nucleotide sequence of SEQ ID NO:15, (H1) an endogenous antisense RNA of mammalian MAPK7 gene comprising a nucleotide sequence the same or substantially the same as the nucleotide sequence of SEQ ID NO:16, (H2) an endogenous antisense RNA of mammalian FGFR4 gene comprising a nucleotide sequence the same or substantially the same as the nucleotide sequence of SEQ ID NO:17, (H3) an endogenous antisense RNA of mammalian thrombospondin 2 gene comprising a nucleotide sequence the same or substantially the same as the nucleotide sequence of SEQ ID NO:18, (H4) an endogenous antisense RNA of mammalian cadherin 13 gene comprising a nucleotide sequence the same or substantially the same as the nucleotide sequence of SEQ ID NO:3, (H5) an endogenous antisense RNA of mammalian cadherin 13 gene comprising a nucleotide sequence the same or substantially the same as the nucleotide sequence of SEQ ID NO:19, (H6) an endogenous antisense RNA of mammalian cadherin 13 gene comprising a nucleotide sequence the same or substantially the same as the nucleotide sequence of SEQ ID NO:20, (H7) an endogenous antisense RNA of mammalian PCNA gene comprising a nucleotide sequence the same or substantially the same as the nucleotide sequence of SEQ ID NO:21, (H8) an endogenous antisense RNA of mammalian PDGFR gene comprising a nucleotide sequence the same or substantially the same as the nucleotide sequence of SEQ ID NO:22, (H9) an endogenous antisense RNA of mammalian cyclin B1 gene comprising a nucleotide sequence the same or substantially the same as the nucleotide sequence of SEQ ID NO:23, (H10) an endogenous antisense RNA of mammalian ERCC3 gene comprising a nucleotide sequence the same or substantially the same as the nucleotide sequence of SEQ ID NO:24, (H11) an endogenous antisense RNA of mammalian CD34 antigen gene comprising a nucleotide sequence the same or substantially the same as the nucleotide sequence of SEQ ID NO:25, (H12) an endogenous antisense RNA of mammalian integrin α6 gene comprising a nucleotide sequence the same or substantially the same as the nucleotide sequence of SEQ ID NO:26.

Any cancer can be diagnosed with an endogenous antisense RNA according to the present invention, as long as the relative expression of the antisense RNA to the corresponding sense RNA changes, preferably decreases, significantly with specificity for the cancer. Preferably, the cancer is exemplified by colorectal cancer in the case of the antisense RNAs (C1) to (C15) described above, and by hepatic cancer in the case of the antisense RNAs (H1) to (H12) described above.

Although any mammal (e.g., humans, mice, rats, monkeys, dogs, bovines, horses, pigs, sheep, goat, rabbits, hamsters and the like) can be the subject of cancer diagnosis using a cancer marker according to the present invention, the subject is preferably a human, mouse, rat, monkey, dog or the like, more preferably a human or mouse.

The nucleotide sequence of SEQ ID NO:1 is an antisense strand sequence of the 244-303rd bases of the cDNA sequence of the human CDK4 gene registered under accession number M14505 with the GenBank database. As shown in an Example below, the human antisense CDK4 according to the present invention (an antisense RNA against the CDK4 gene; hereinafter, similar abbreviations are sometimes used to denote antisense RNAs for other genes) is hybridizable with a 60mer nucleotide sequence complementary to the nucleotide sequence of SEQ ID NO:1. Therefore, the human antisense CDK4 is an RNA having a nucleotide sequence comprising at least all or a portion of the nucleotide sequence of SEQ ID NO:1.

The nucleotide sequence of SEQ ID NO:16 is an antisense strand sequence of the 1709-1768th bases of the cDNA sequence of the human MAPK7 gene registered under accession number U25278 with the GenBank database. As shown in an Example below, the human antisense MAPK7 according to the present invention is hybridizable with a 60mer nucleotide sequence complementary to the nucleotide sequence of SEQ ID NO:16. Therefore, the human antisense MAPK7 is an RNA having a nucleotide sequence comprising at least all or a portion of the nucleotide sequence of SEQ ID NO:16.

Similarly, the nucleotide sequence of SEQ ID NO:2 is a portion of an antisense strand sequence of a cDNA sequence of a human MAPK9 (mutagen-activated protein kinase 9) gene deposited in the GenBank database under Accession No. L31951.

The nucleotide sequence of SEQ ID NO:3 is a portion of an antisense strand sequence of a cDNA sequence of a human cadherin 13 (cadherin 13, H-cadherin (heart)) gene deposited in the GenBank database under Accession No. L34058.

The nucleotide sequence of SEQ ID NO:4 is a portion of an antisense strand sequence of a cDNA sequence of a human cyclin B1 (Cycline B1) gene deposited in the GenBank database under Accession No. M25753.

The nucleotide sequence of SEQ ID NO:5 is a portion of an antisense strand sequence of a cDNA sequence of a human pLK (Polo-like kinase (*Drosophila*)) gene deposited in the GenBank database under Accession No. U01038.

The nucleotide sequence of SEQ ID NO:6 is a portion of an antisense strand sequence of a cDNA sequence of a human RHAMM (hyaluronan-mediated motility receptor) gene deposited in the GenBank database under Accession No. U29343.

The nucleotide sequence of SEQ ID NO:7 is a portion of an antisense strand sequence of a cDNA sequence of a human β3-endonexin (integrin beta 3 binding protein (beta 3-endonexin)) gene deposited in the GenBank database under Accession No. U37139.

The nucleotide sequences of SEQ ID NOs:8 and 9 are each a portion of an antisense strand sequence of a cDNA sequence of a human BRCA2 (Breast cancer 2, early onset) gene deposited in the GenBank database under Accession No. U43746.

The nucleotide sequence of SEQ ID NO:10 is a portion of an antisense strand sequence of a cDNA sequence of a human BBP/53BP2 (tumor protein p53 binding protein, 2) gene deposited in the GenBank database under Accession No. U58334.

The nucleotide sequence of SEQ ID NO:11 is a portion of an antisense strand sequence of a cDNA sequence of a human type IV collagen α3 (collagen, type VI, alpha 3) gene deposited in the GenBank database under Accession No. X52022.

The nucleotide sequence of SEQ ID NO:12 is a portion of an antisense strand sequence of a cDNA sequence of a human MMP11 (matrix metalloproteinase 11 (stromelysin 3) gene deposited in the GenBank database under Accession No. X57766).

The nucleotide sequences of SEQ ID NOs:13, 14 and 15 are each a portion of an antisense strand sequence of a cDNA sequence of a human P-cadherin (cadherin 3, type 1, P-cadherin (placental) gene deposited in the GenBank database under Accession No. X63629).

The nucleotide sequence of SEQ ID NO:17 is a portion of an antisense strand sequence of a cDNA sequence of a human FGFR4 (fibroblast growth factor receptor 4) gene deposited in the GenBank database under Accession No. L03840.

The nucleotide sequence of SEQ ID NO:18 is a portion of an antisense strand sequence of a cDNA sequence of a human thrombospondin 2 (thrombospondin 2) gene deposited in the GenBank database under Accession No. L12350.

The nucleotide sequences of SEQ ID NOs:19 and 20 are each a portion of an antisense strand sequence of a cDNA sequence of a human cadherin 13 (cadherin13, H-cadherin (heart)) gene deposited in the GenBank database under Accession No. L34058.

The nucleotide sequence of SEQ ID NO:21 is a portion of an antisense strand sequence of a cDNA sequence of a human PCNA (proliferating cell nuclear antigen) gene deposited in the GenBank database under Accession No. M15796.

The nucleotide sequence of SEQ ID NO:22 is a portion of an antisense strand sequence of a cDNA sequence of a human PDGFR (platelet-derived growth factor receptor, beta polypeptide) gene deposited in the GenBank database under Accession No. M21616.

The nucleotide sequence of SEQ ID NO:23 is a portion of an antisense strand sequence of a CDNA sequence of a human cyclin B1 (Cyclin B1) gene deposited in the GenBank database under Accession No. M25753.

The nucleotide sequence of SEQ ID NO:24 is a portion of an antisense strand sequence of a cDNA sequence of a human ERCC3 (excision repair cross-complementing rodent repair deficiency, complementation group 3 (xeroderma pigmentosum group B complementing)) gene deposited in the GenBank database under Accession No. M31899.

The nucleotide sequence of SEQ ID NO:25 is a portion of an antisense strand sequence of a cDNA sequence of a human CD34 antigen (CD34 antigen) gene deposited in the GenBank database under Accession No. M81104.

The nucleotide sequence of SEQ ID NO:26 is a portion of an antisense strand sequence of a cDNA sequence of a human integrin α6 (integrin, alpha 6) gene deposited in the GenBank database under Accession No. X53586.

As shown in an Example below, a human antisense RNA according to the present invention is hybridizable with a 60 mer nucleotide sequence complementary to the nucleotide sequence shown by each sequence identification number. Therefore, the human antisense RNA is an RNA having a nucleotide sequence comprising at least all or a portion of the nucleotide sequence shown by each sequence identification number.

"Substantially the same nucleotide sequence as the nucleotide sequence of SEQ ID NO:n (n=1 to 26; the same applies below)" means a fragment of the nucleotide sequence of SEQ ID NO:n, the nucleotide sequence of the region corresponding to SEQ ID NO:n, of an antisense strand sequence of a cDNA sequence of each gene ortholog in a non-human mammal, or a naturally occurring allelic variant or polymorph thereof.

A cancer marker antisense RNA according to the present invention can be detected by a method of RNA detection known per se using a nucleic acid comprising a nucleotide sequence hybridizable therewith as the probe or primer.

Therefore, the present invention also provides a cancer diagnostic reagent containing a nucleic acid comprising a nucleotide sequence hybridizable with a cancer marker antisense RNA. Although any cancer can be diagnosed using the diagnostic reagent, as long as the relative expression of the above-described antisense RNA to the corresponding sense RNA changes, preferably decreases, significantly with specificity for the cancer. Preferably, the cancer is exemplified by colorectal cancer in the case of a reagent containing a nucleic acid comprising a nucleotide sequence hybridizable with any of the antisense RNAs (C1) to (C15) described above, and by hepatic cancer in the case of an antisense RNA for any of the antisense RNAs (H1) to (H12) described above.

The nucleic acid for detection of a cancer marker antisense RNA of the present invention is not particularly limited as long as it is a nucleic acid comprising a nucleotide sequence hybridizable to a target antisense RNA sequence under the hybridization conditions usable for general gene expression analyses. Preferably, the probe is a nucleic acid comprising a nucleotide sequence hybridizable to a target antisense RNA sequence under stringent conditions. The "stringent conditions" mean the conditions under which only a nucleotide sequence having 95% or more, preferably 96% or more, more preferably 97% or more, particularly preferably 98% or more, most preferably 99% or more homology to a nucleotide sequence completely complementary to the target nucleotide sequence is hybridizable. Those of ordinary skill in the art can easily control the conditions to have desired stringency by appropriately changing the salt concentration of hybridization solution, temperature of hybridization reaction, probe concentration, probe length, number of mismatches, hybridization reaction time, salt concentration of washing solution, temperature of washing step and the like.

Examples of the nucleic acid used to detect a cancer marker antisense RNA according to the present invention include a nucleic acid probe hybridizable specifically with the antisense RNA to be detected, and a pair of oligonucleotides capable of functioning as primers to amplify a portion or all of the antisense RNA. The nucleic acid may be DNA or RNA, or a DNA/RNA chimera, with preference given to DNA.

The nucleic acid used as a probe may be double-stranded or single-stranded. If double-stranded, the nucleic acid may be a double-stranded DNA, a double-stranded RNA, or a DNA: RNA hybrid. The nucleic acid may be of any length allowing specific hybridization thereof with the target antisense RNA; for example, the length is about 15 bases or more, preferably about 30 bases or more. The nucleic acid is preferably labeled with a labeling agent to enable the detection and quantitation of the target nucleic acid. As the labeling agent, for example, radioisotope, enzyme, fluorescent substance, luminescent substance and the like are used. As the radioisotope, for example, [$^{32}$P], [$^{3}$H], [$^{14}$C] and the like are used. As the enzyme, a stable enzyme showing high specific activity is preferable and, for example, β-galactosidase, β-glucosidase, alkaline phosphatase, peroxidase, malate dehydrogenase and the like are used. As the fluorescent-substance, for example, fluorescamine, fluorescein isothiocyanate and the like are used. As the luminescent substance, for example, luminol, luminol derivative, luciferin, lucigenin and the like are used. Moreover, biotin-(strept)avidin can be used for binding a probe and a labeling agent. In addition, when a nucleic acid to be the probe is to be immobilized on a solid phase, a nucleic acid in a sample can be labeled using a labeling agent similar to those mentioned above.

The set of oligonucleotides used as primers may be any set of oligonucleotides that are specifically hybridizable with the sense strand and antisense strand, respectively, of a double-stranded DNA synthesized from an antisense RNA comprising the nucleotide sequence of SEQ ID NO:n using a method known per se, and that are capable of amplifying the DNA fragment positioned therebetween. Examples of such sets of oligonucleotides include a set of oligo-DNAs each having a length of about 15 to about 100 bases, preferably about 15 to about 50 bases, and designed to amplify a DNA fragment about 100 bp to several kbp long.

A nucleic acid that can function as a probe to detect a cancer marker antisense RNA according to the present invention can be acquired by amplifying a nucleic acid of desired length by an RT-PCR method using a primer set capable of amplifying a portion or all of the antisense RNA, with a total RNA derived from optionally chosen mammalian cells [e.g., hepatocytes, splenocytes, nerve cells, glial cells, pancreatic P cells, bone marrow cells, mesangial cells, Langerhans cells, epidermal cells, epithelial cells, goblet cells, endothelial cells, smooth muscle cells, fibroblast, fiber cells, muscle cells, adipocytes, immune cells (e.g., macrophage, T cell, B cell, natural killer cell, mast cell, neutrophil, basophil, eosinophil, monocyte), megakaryocytes, synovial cells, chondrocytes, osteocytes, osteoblasts, osteoclasts, mammary cells, hepatocytes, interstitial cells, and precursor cells, stem cells, cancer cells and the like of these cells] or any tissues where those cells are present [e.g., brain, each moiety of the brain (e.g., olfactory bulb, amygdaloid nucleus, basal ganglia, hippocampus, thalamus, hypothalamus, cerebral cortex, medulla oblongata, cerebellum), spinal cord, pituitary gland, stomach, pancreas, kidney, liver, gonad, thyroid gland, gall bladder, bone marrow, adrenal gland, skin, lung, gastrointestinal tracts (e.g., large intestine, small intestine), blood vessel, heart, thymus, spleen, submandibular gland, peripheral blood, prostate, orchis, ovary, placenta, uterus, bone, joint, adipose tissue, skeletal muscle and the like] as the template. Alternatively, the nucleic acid can also be obtained by chemically synthesizing a portion or all of the nucleotide sequence and/or a complementary strand sequence thereof, using a commercially available DNA/RNA synthesizer and the like, on the basis of nucleotide sequence information on the sense RNA (cDNA) corresponding to the cancer marker antisense RNA according to the present invention (e.g., the nucleotide sequences of human CDK4 and human MAPK7 are registered under accession numbers M14505 and U25278, respectively, with the GenBank database). By direct in situ (on chip) synthesis of the nucleic acid on a solid phase such as silicone or glass, a chip (array) having the nucleic acid immobilized thereon may be prepared.

These nucleic acids can be provided in a solid form as a dried product or alcohol precipitate, and can also be provided in solution in water or an appropriate buffer solution (e.g., TE buffer solution). When used as a labeled probe, the nucleic acid can be provided in a state previously labeled with any one of the above-described labels, and can also be provided separately from the label and may be labeled before use.

Alternatively, the nucleic acid can also be provided in a state immobilized on an appropriate solid phase. Examples of solid phases include, but are not limited to, glass, silicone, plastics, nitrocellulose, nylon, and polyvinylidene difluoride. Examples of the immobilization means include, but are not limited to, a method comprising introducing a functional group such as amino group, aldehyde group, SH group, biotin and the like into a nucleic acid in advance, introducing a functional group (e.g., aldehyde group, amino group, SH group, streptavidin and the like) that can react with the nucleic acid, on a solid phase, and crosslinking the solid phase and the nucleic acid by a covalent bond between both functional groups, or coating a solid phase with a polycation and immobilizing a polyanionic nucleic acid by utilizing an electrostatic bond, and the like.

One preferable example of nucleic acid probes immobilized on a solid phase is DNA microarray. Examples of the preparation method of DNA microarray include the Affymetrix type wherein a nucleic acid probe is synthesized by a photolithography method synthesizing nucleotide one by one on a substrate (glass, silicone and the like), and the Stanford type wherein a nucleic acid probe prepared in advance is spotted onto a substrate by a microspotting method, an inkjet method, a bubble jet (registered trademark) method and the like. When a probe of 30mer or more is used, the Stanford type or a combination of the two types is preferable.

To quantitatively analyze the expression of a cancer marker antisense RNA according to the present invention using a very small amount of RNA sample, it is preferable that competitive RT-PCR or real-time RT-PCR be used. In competitive RT-PCR, the amount of desired DNA is determined by allowing a known amount of another template nucleic acid that can be amplified by a set of primers capable of amplifying the desired DNA, as the competitor, to coexist in the reaction liquid to cause a competitive amplification reaction, and comparing the amounts of the amplification products. Therefore, when competitive RT-PCR is used, a reagent according to the present invention may further comprise a nucleic acid that produces an amplification product amplified by the primer set, and distinct from the desired DNA (for example, an amplification product having a size different from that of the desired DNA, an amplification product exhibiting a different migration pattern with restriction endonuclease treatment), in addition to the primer set described above. This competitor nucleic acid may be DNA or RNA. In the case of DNA, PCR may be performed with the addition of the competitor after a cDNA is synthesized from an RNA sample by a reverse transcription reaction. In the case of RNA, RT-PCR can be performed with the addition of the competitor without synthesis of a cDNA. In the latter case, the absolute amount of the original mRNA can be estimated because the reverse transcription reaction efficiency is also taken into consideration.

On the other hand, real-time RT-PCR obviates electrophoresis because of its capability of monitoring the amount of PCR amplification in real time, thus enabling quicker analysis of the expression of a cancer marker antisense RNA according to the present invention. Usually, this monitoring is performed using a variety of fluorescent reagents, including reagents that emit fluorescence by binding to double-strand DNA, such as SYBR Green I and ethidium bromide (intercalating agent), as well as a nucleic acid that can be used as the above-described probe (however, the nucleic acid hybridizes with the target nucleic acid in the amplification region) modified at both ends thereof with a fluorescent substance (e.g., FAM, HEX, TET, FITC) and a quencher (e.g., TAMRA, DABCYL), respectively, and the like.

The present invention also provides a testing method for cancer diagnosis, comprising measuring the amount of a cancer marker antisense RNA according to the present invention in an RNA-containing sample collected from a subject mammal using a nucleic acid capable of detecting the cancer marker antisense RNA.

Examples of an RNA-containing sample collected from a test mammal, any cells [e.g., hepatocytes, splenocytes, nerve cells, glial cells, pancreatic β cells, bone marrow cells, mesangial cells, Langerhans cells, epidermal cells, epithelial cells, goblet cells, endothelial cells, smooth muscle cells, fibroblast, fiber cells, muscle cells, adipocytes, immune cells (e.g., macrophage, T cell, B cell, natural killer cell, mast cell, neutrophil, basophil, eosinophil, monocyte), megakaryocytes, synovial cells, chondrocytes, osteocytes, osteoblasts, osteoclasts, mammary cells, interstitial cells, and precursor cells, stem cells, cancer cells and the like of these cells] or any tissues where those cells are present [e.g., brain, each moiety of the brain (e.g., olfactory bulb, amygdaloid nucleus, basal ganglia, hippocampus, thalamus, hypothalamus, cerebral cortex, medulla oblongata, cerebellum), spinal cord, eyeball, pituitary gland, stomach, pancreas, kidney, liver, gonad, thyroid gland, gall bladder, bone marrow, adrenal gland, skin, lung, gastrointestinal tracts (e.g., large intestine, small intestine), blood vessel, heart, thymus, spleen, submandibular gland, peripheral blood, prostate, orchis, ovary, placenta, uterus, bone, joint, adipose tissue, skeletal muscle and the like], and the like. As long as antisense RNA to be detected can be expressed, blood (e.g., peripheral blood), lymphocytes and the like are preferable since they can be recovered quickly and conveniently, and are less-invasive to animals.

The expression of the antisense RNA in the cell-containing sample collected from the subject mammal's cell can be examined by preparing a total RNA fraction from the sample, and detecting the marker antisense RNA contained in the fraction. The RNA fraction can be prepared using commonly known techniques such as guanidine-CsCl ultracentrifugation and the AGPC method, but highly pure total RNA can be prepared from a very small amount of sample quickly and conveniently using a commercially available RNA extraction kit (e.g., RNeasy Mini Kit; manufactured by QIAGEN). Examples of means of detecting the gene transcription product in the RNA fraction include a method based on hybridization (Northern blotting, dot blotting, DNA chip (microarray) analysis and the like) and a method based on PCR (RT-PCR, competitive PCR, real-time PCR and the like). Because a change in gene expression can be detected quickly and conveniently at high quantitative analyzability with a very small amount of sample, quantitative PCR methods such as competitive PCR and real-time PCR are preferable. DNA chip (microarray) analysis is preferable because changes in the expression of a plurality of marker genes can be detected at one time, and also because the quantitative analyzability can be improved by choosing an appropriate method of detection.

When Northern blot or dot blot hybridization is used, the expression of an antisense RNA can be detected using a diagnostic reagent according to the present invention described above, comprising a nucleic acid used as a labeled probe. When Northern hybridization is used, an RNA fraction prepared as described above is separated by gel electrophoresis, after which the fraction is transferred onto a membrane such as of nitrocellulose, nylon, or polyvinylidene difluoride, and hybridized in a hybridization buffer solution containing a reagent according to the present invention, preferably under the "stringent conditions" described above, after which the amount of label bound to the membrane is measured for each band by an appropriate method, whereby the expression level of each gene can be measured. In the case of dot blotting, the membrane having the RNA fraction spotted thereon is subjected to a hybridization reaction in the same way (performed for each antisense RNA), and the amount of spot labeled is measured, whereby the expression level of each antisense RNA can be measured.

When DNA chip (microarray) analysis is performed, for example, a cDNA harboring a suitable promoter such as T7 promoter and the like is synthesized by reverse transcription reaction from the RNA fraction prepared as mentioned above, and a cRNA is synthesized using an RNA polymerase (labeled cRNA is obtained here by using, as a substrate, mononucleotide labeled with biotin and the like). The labeled cRNA is contacted with the above-mentioned solid-phased probe to perform a hybridization reaction, and the label bound with each probe on the solid phase is quantified to determine the level of expression of each antisense RNA.

In the method according to the present invention, a judgment to determine whether a subject mammal is suffering from a cancer (or is likely to suffer from a cancer in the future) can be made by, for example, measuring the expression level of a cancer marker antisense RNA according to the present invention in an RNA-containing sample collected from a healthy control mammal in the same manner, and comparing the expression of the antisense RNA between the subject and control animals. If the expression of the antisense RNA has changed significantly in the subject animal compared with the control animal, preferably has decreased significantly in the subject animal, the subject animal can be judged to be suffering from a cancer (or to be likely to suffer from a cancer in the future).

The diagnostic method according to the present invention can comprise detecting the expression of an mRNA transcribed by a sense strand corresponding to an antisense RNA. The expression balance between the sense and antisense RNAs is compared between a subject animal and a control animal. If the expression balance has changed significantly between the subject and control animals, preferably if the expression of the antisense RNA is higher than the expression of the sense strand in the control animal, whereas the expression of the antisense RNA has decreased compared with the expression of the sense strand in the subject animal, the subject animal can be judged to be suffering from a cancer (or to be likely to suffer from a cancer in the future).

The cancer marker antisense RNAs according to the present invention negatively control the expression of the oncogenes CDK4 and MAPK7; it is thought that in cancer patients, the expression of oncogene products has increased synergistically because not only the gene expression of the sense strand has increased, but also the expression of these endogenous antisense RNAs have decreased remarkably. Therefore, a nucleic acid comprising all or a portion of the nucleotide sequence of one of these endogenous antisense RNAs is expected to be effective in suppressing the expression of the CDK4 and MAPK7 proteins in cancer patients, as are antisense pharmaceuticals and RNAi pharmaceuticals. Such nucleic acids that mimic endogenous antisense RNAs are expected to be superior to antisense or RNAi pharmaceuticals designed artificially on the basis of sequence information, in terms of translation suppressive effect, reductions in adverse reactions, improvements of in vivo kinetics and other aspects.

The present invention is explained in more detail in the following by referring to Examples, which are mere exemplification and are not to be construed as limitative.

EXAMPLE 1

Production of Microarray

Using a gene-specific 60mer oligo DNA probe and a system of Agilent Technologies Inc., a custom-made microarray was prepared. As the probe, a probe of a gene sequence (sense strand) used for cancer research and its antisense strand probe were placed on the microarray. As for the antisense strand probe, a complementary strand sequence of the cDNA sequence of the gene was prepared, and specific 60mer was selected and placed on the array. As a result of cDNA sequence analysis, the antisense strand probes also contained antisense strand probes of the gene for which the antisense strand corresponding to the sense strand was not found.

EXAMPLE 2

Expression Analysis

Using the microarray chip of Example 1, the expression in a cancer sample was analyzed. As an oligo(dT) label for the sample, a labeling kit and a fluorescence dye (Cy3) for a single-dye method as specified by Agilent Technologies Inc. were used, and a target cRNA was produced and hybridized. For a random priming method, a target cDNA was prepared using a CyScribe First-Strand cDNA Labeling Kit (Amersham) and hybridized. The hybridization and washing were performed according to the protocol recommended by Agilent Technologies Inc.

After the hybridization, the fluorescence intensity on the slide glass was measured by a scanner of Agilent Technologies Inc., and the data was corrected using a software (Feature Extraction) provided by Agilent Technologies Inc. to give a signal value (processed signal).

Based on the above data, the signal ratios of the sense strand and the antisense strand were compared between the disease sample and a normal tissue, whereby the antisense RNA that is expressed disease-specifically was identified.

(1) Expression Analysis of Colorectal Cancer Sample

The expression of the sense strand and the antisense strand of 12 genes, which are known to show increased expression in colorectal cancer, was analyzed according to the above-mentioned method. The probes used were nucleotide sequences complementary to the nucleotide sequences shown by the respective sequence identification numbers listed in Table 1 in order to target the nucleotide sequences as a sense strand and antisense strand, respectively.

TABLE 1

| gene name | GenBank ID | sense strand | antisense strand |
|---|---|---|---|
| CDK4 | M14505 | SEQ ID NO:27 | SEQ ID NO:1 |
| MAPK9 | L31951 | SEQ ID NO:28 | SEQ ID NO:2 |
| cadherin 13 | L34058 | SEQ ID NO:29 | SEQ ID NO:3 |
| cyclin B1 | M25753 | SEQ ID NO:30 | SEQ ID NO:4 |
| pLK | U01038 | SEQ ID NO:31 | SEQ ID NO:5 |
| RHAMM | U29343 | SEQ ID NO:32 | SEQ ID NO:6 |
| β3-endonexin | U37139 | SEQ ID NO:33 | SEQ ID NO:7 |
| BRCA2 | U43746 | SEQ ID NO:34 | SEQ ID NO:8 |

TABLE 1-continued

| gene name | GenBank ID | sense strand | antisense strand |
|---|---|---|---|
| BRCA2 | U43746 | SEQ ID NO:34 | SEQ ID NO:9 |
| BBP/53BP2 | U58334 | SEQ ID NO:35 | SEQ ID NO:10 |
| Type IV collagen α3 | X52022 | SEQ ID NO:36 | SEQ ID NO:11 |
| MMP11 | X57766 | SEQ ID NO:37 | SEQ ID NO:12 |
| P-cadherin | X63629 | SEQ ID NO:38 | SEQ ID NO:13 |
| P-cadherin | X63629 | SEQ ID NO:38 | SEQ ID NO:14 |
| P-cadherin | X63629 | SEQ ID NO:38 | SEQ ID NO:15 |

As the samples, cancer tissues obtained from surgery of six colorectal cancer patients, and the surrounding normal tissues thereof were used, and RNA was extracted by the guanidinium-thiocyanate-phenol-chloroform method using Trizol (Invitrogen) and the like.

Figure 2:
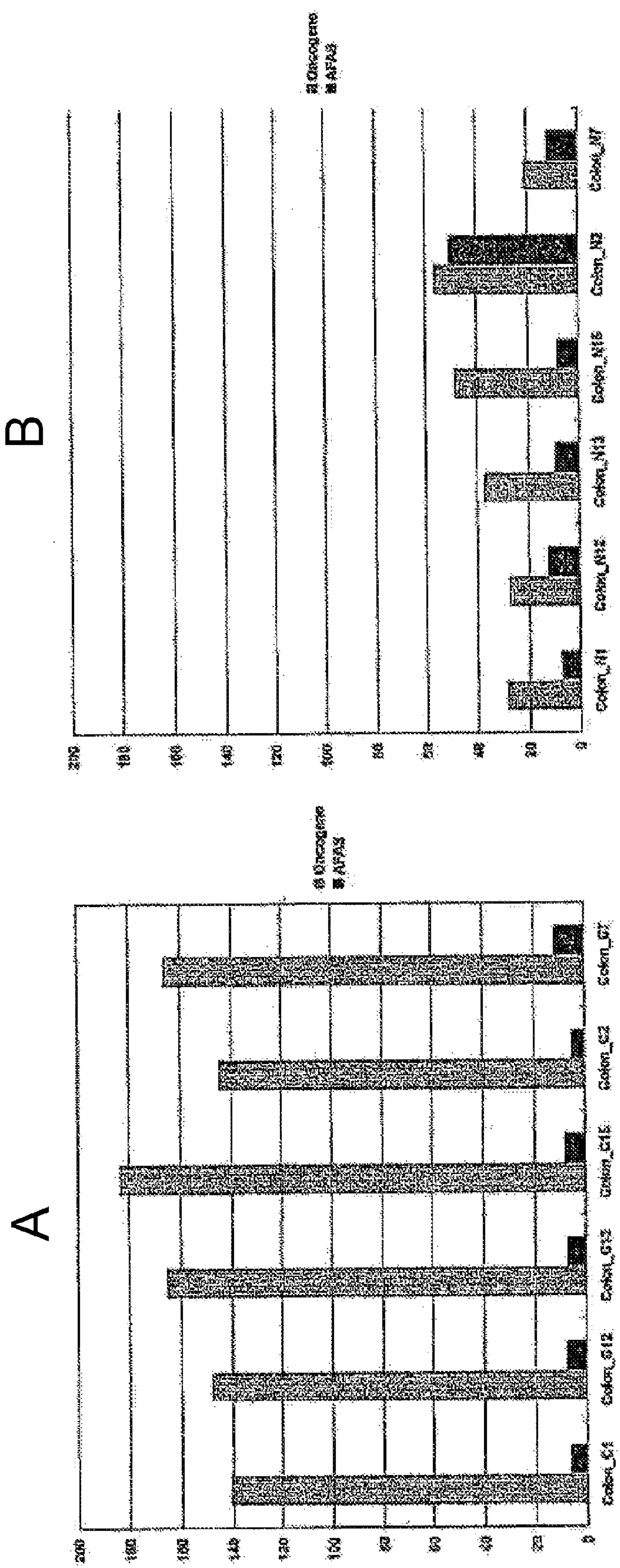
FIG. 2 shows the expression of MAPK9 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 3:
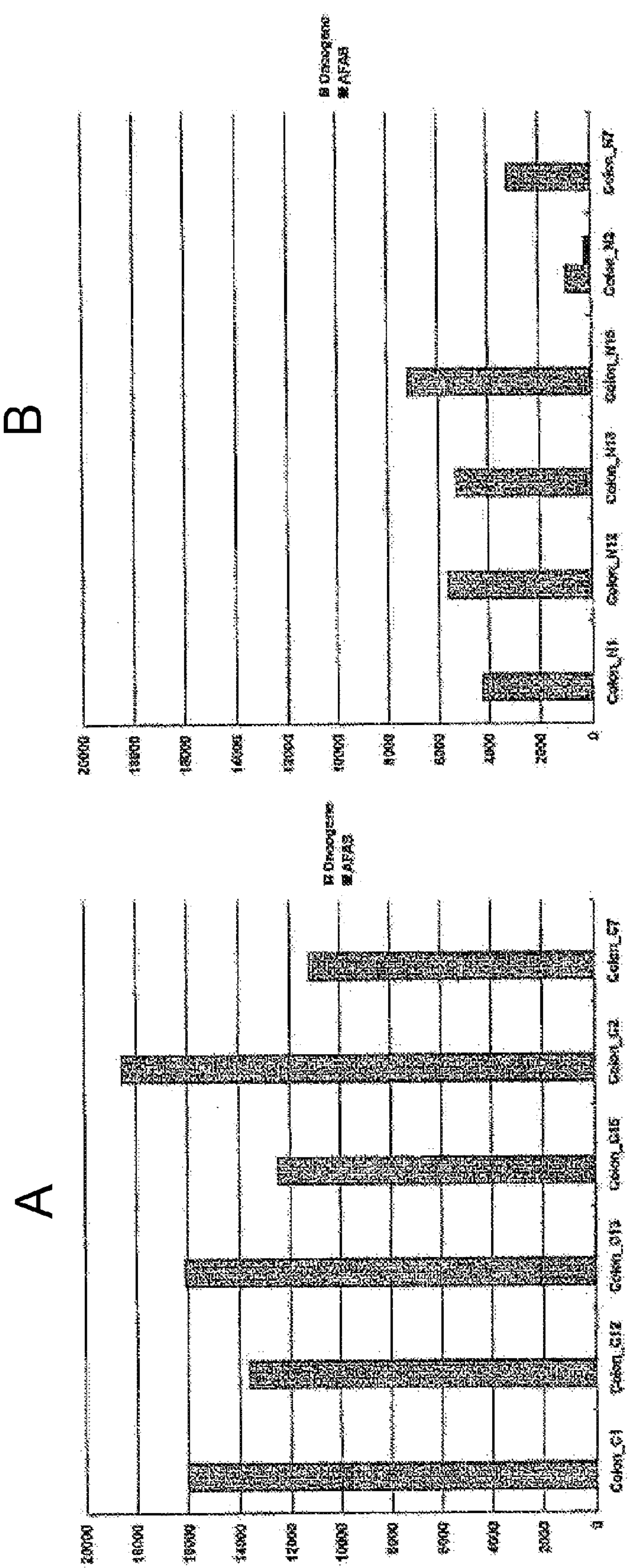
FIG. 3 shows the expression of cadherin 13 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 3:
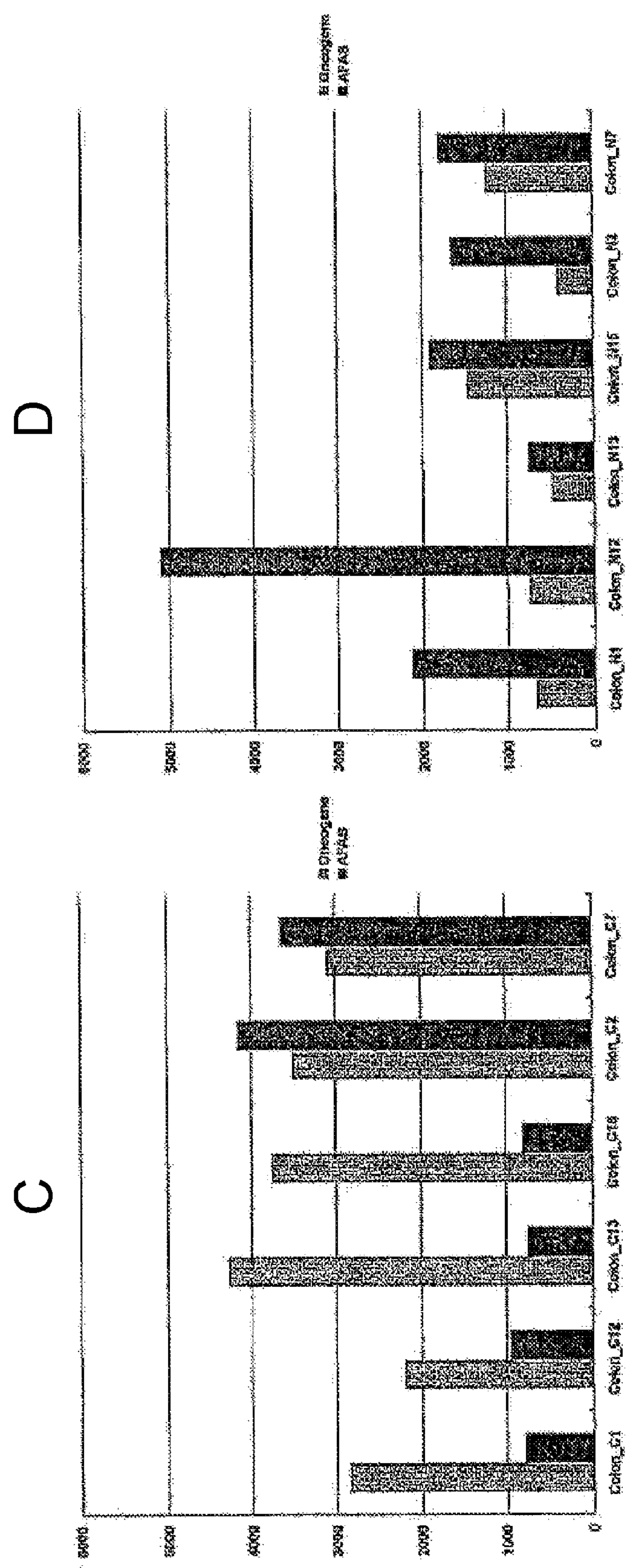
Figure 4:
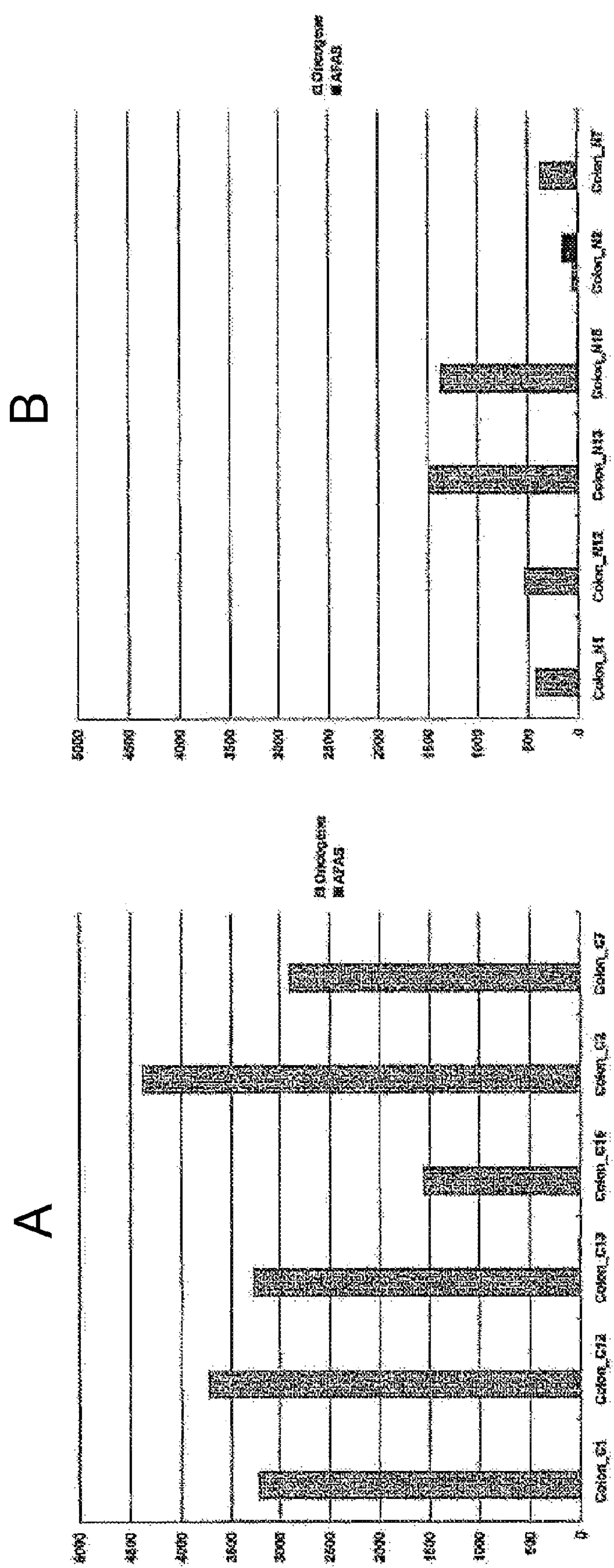
FIG. 4 shows the expression of cyclin B1 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 5:
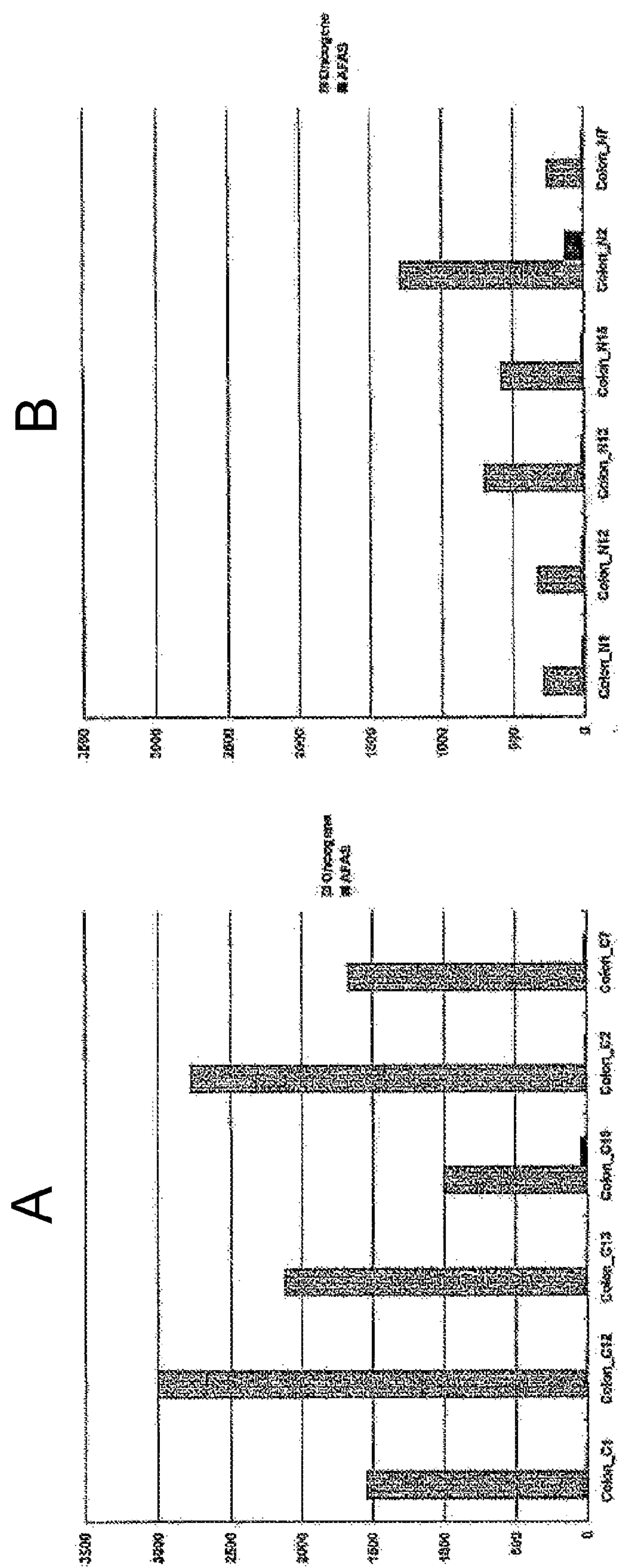
FIG. 5 shows the expression of pLK in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 5:
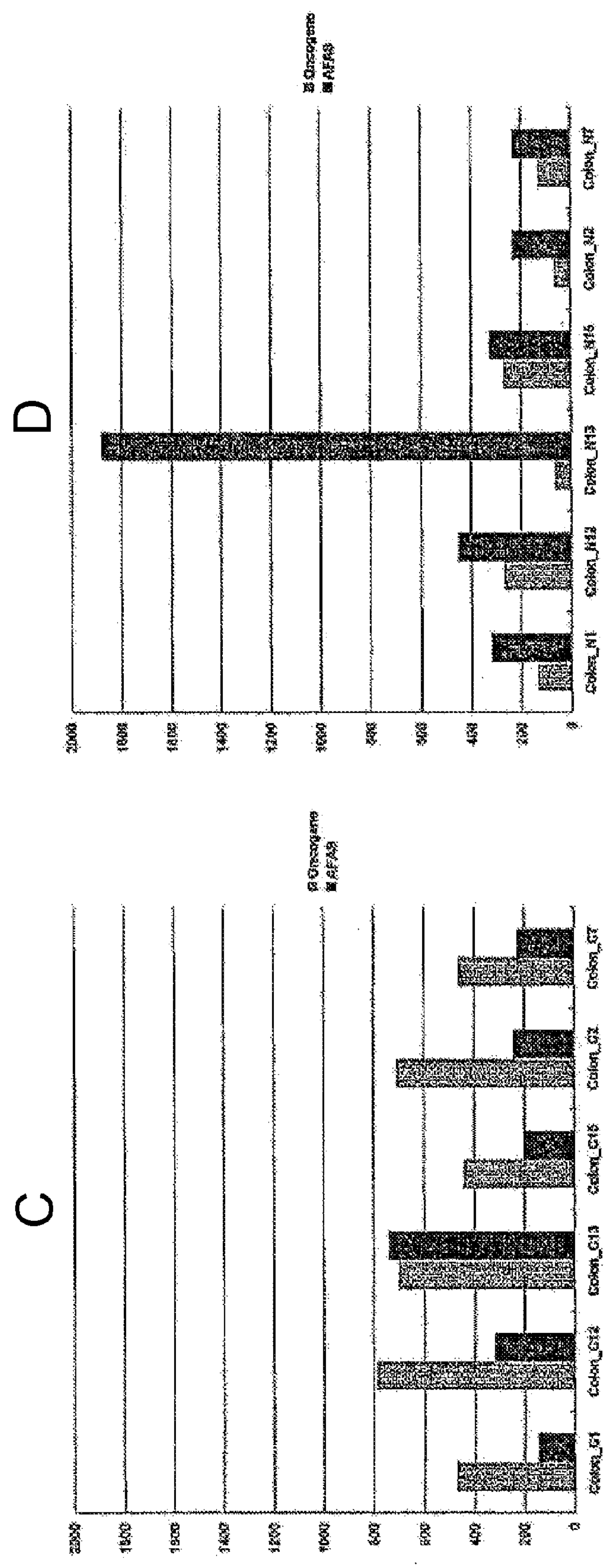
Figure 6:
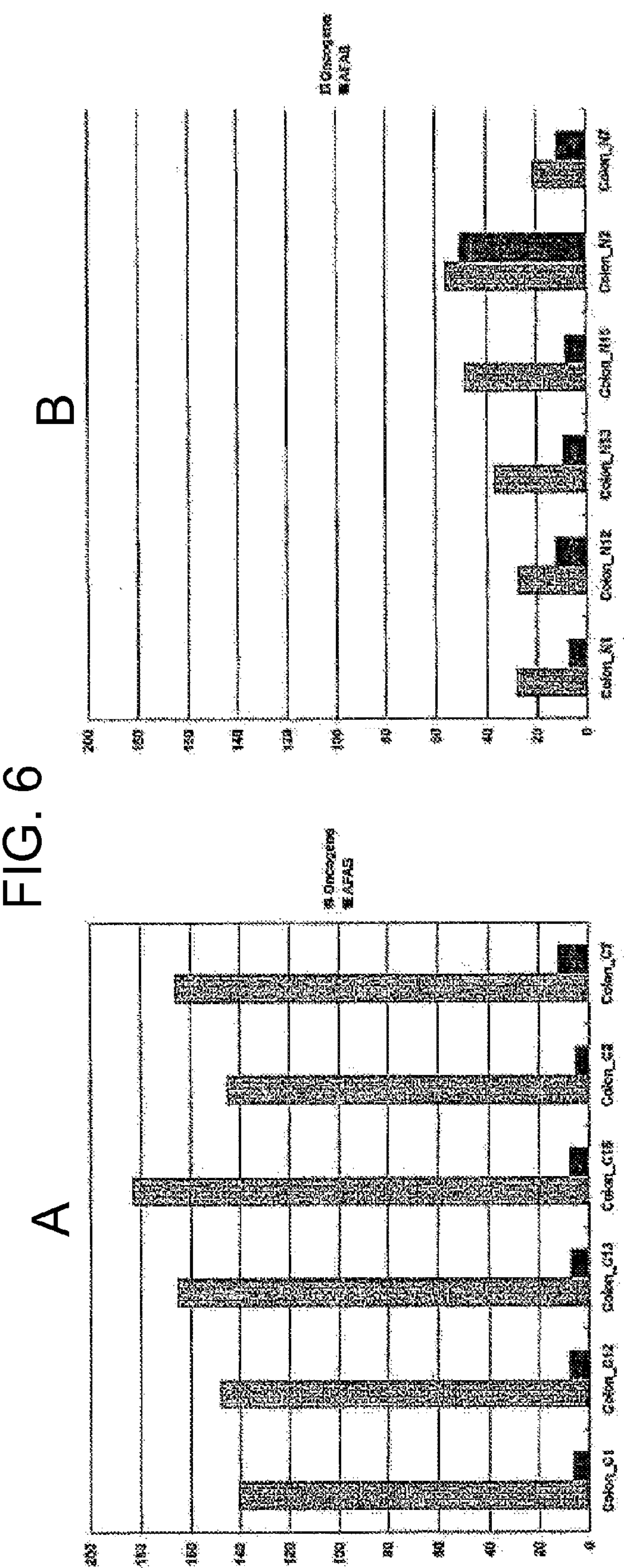
FIG. 6 shows the expression of RHAMM in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 7:
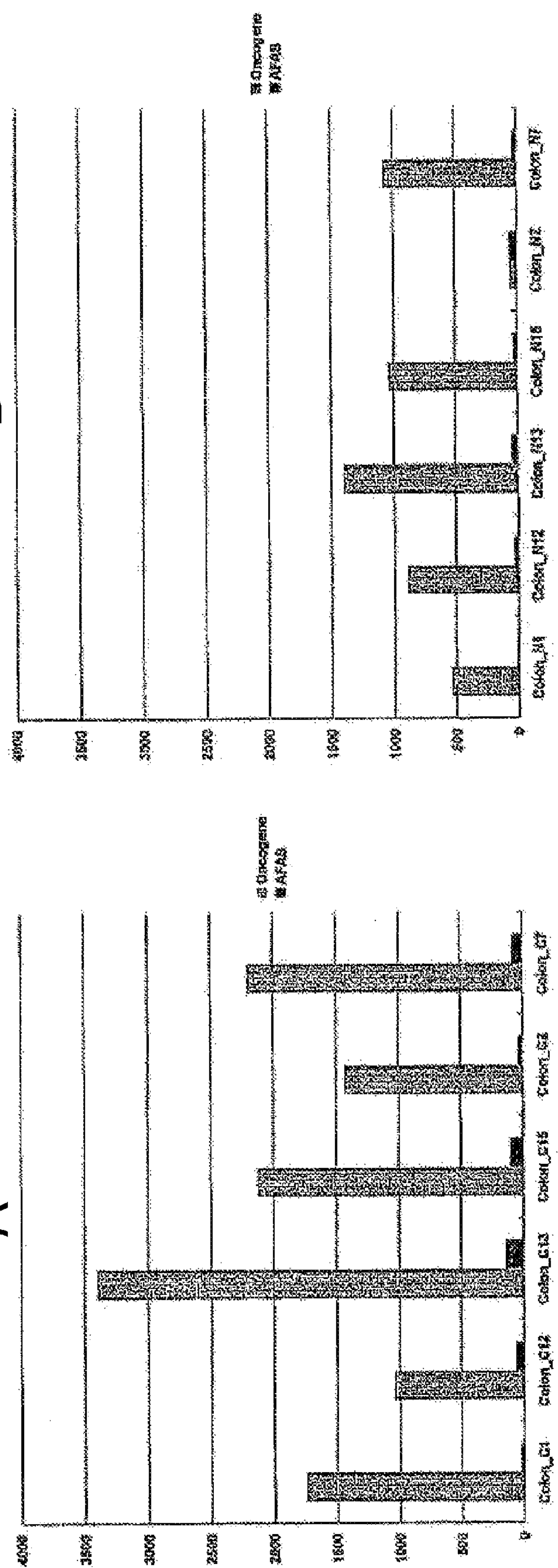
FIG. 7 shows the expression of β3-endonexin in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 7:
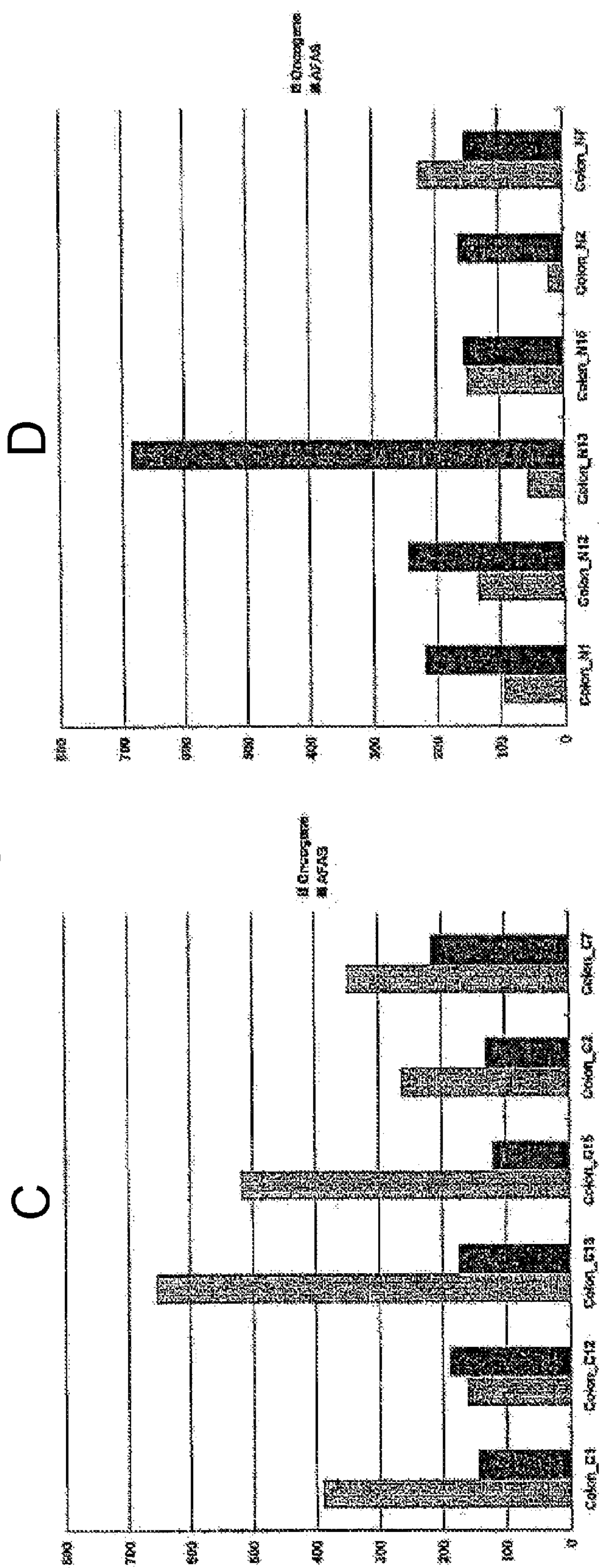
Figure 8:
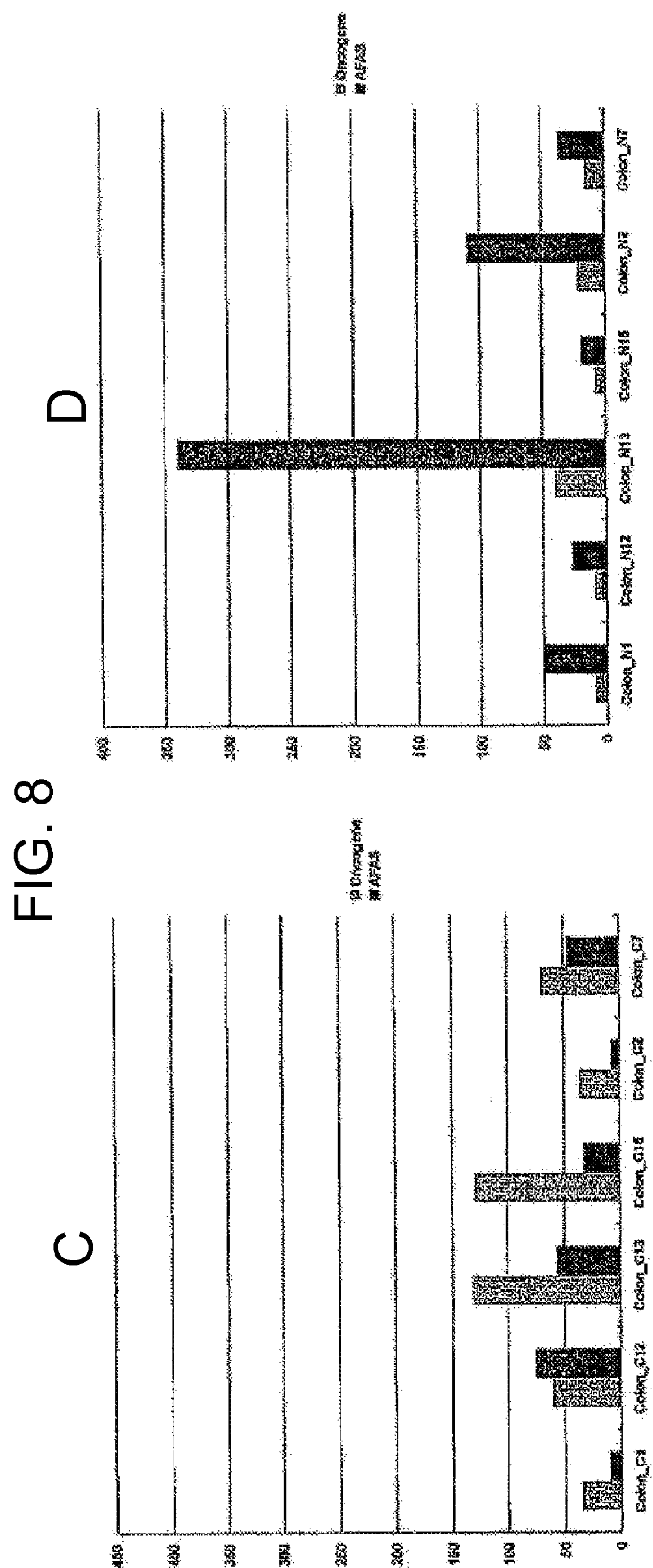
FIG. 8 shows the expression of BRCA2 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 9:
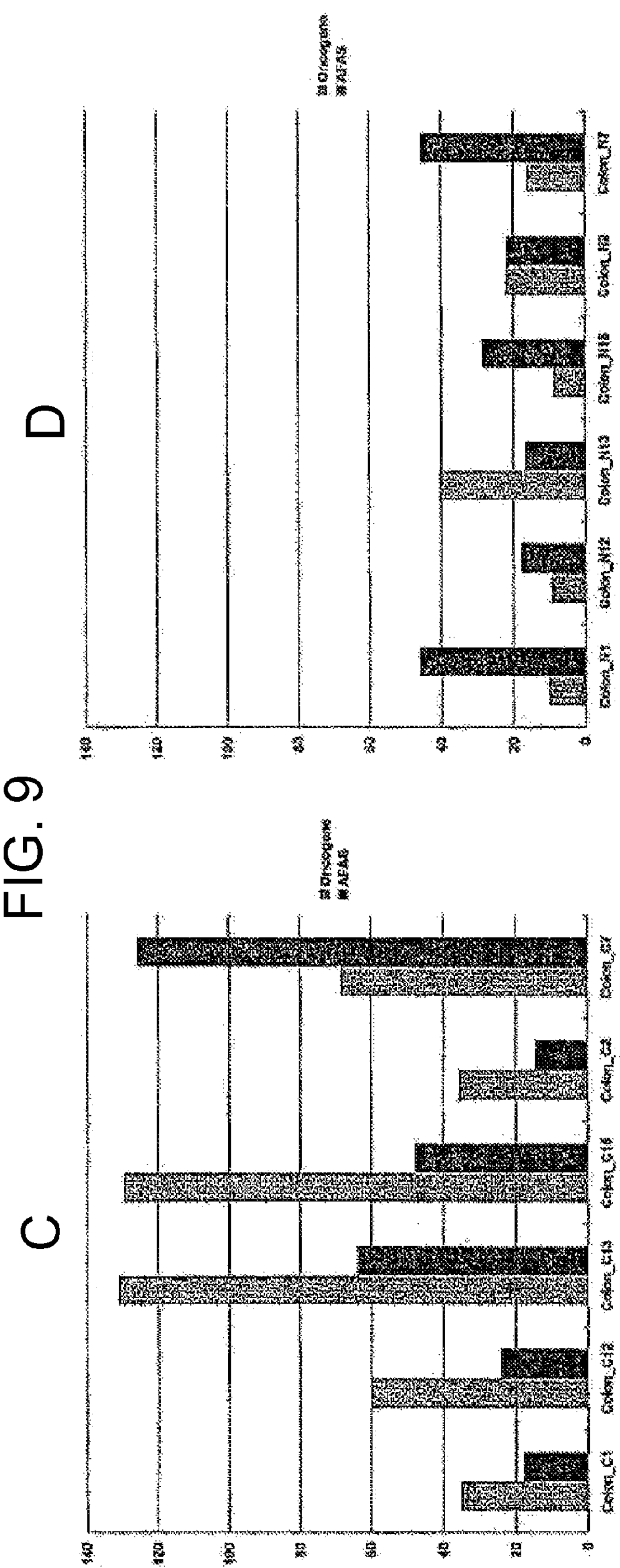
FIG. 9 shows the expression of BRCA2 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 10:
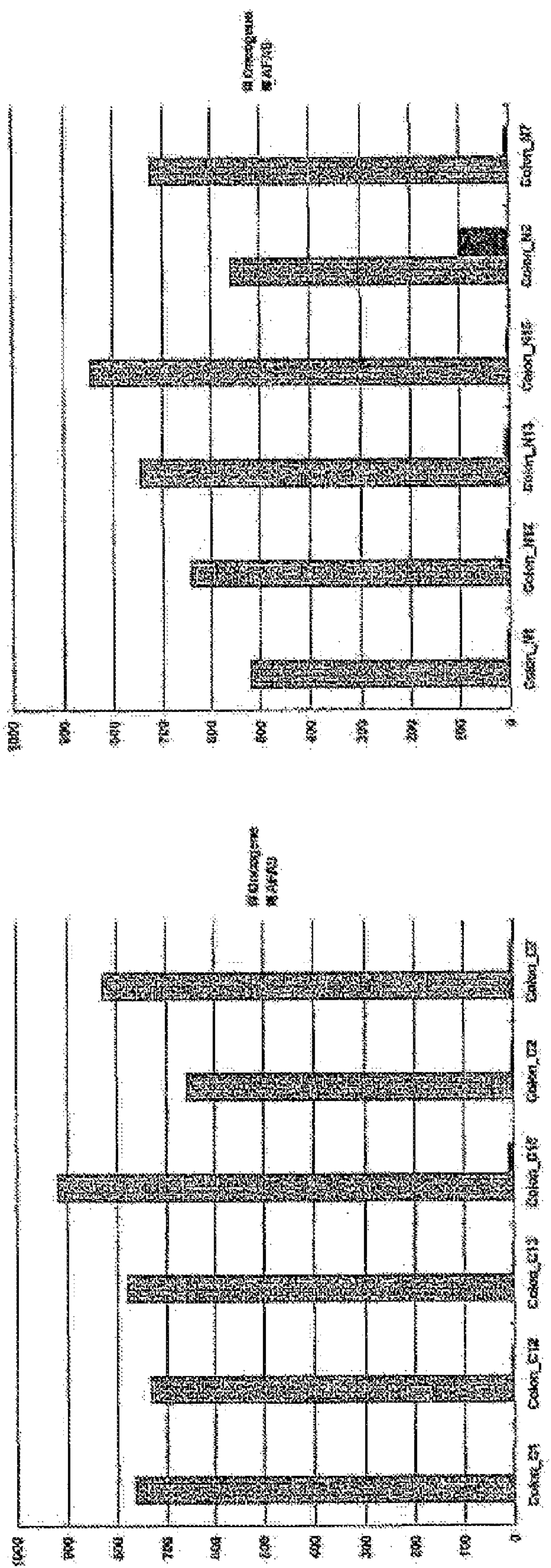
FIG. 10 shows the expression of BBP/53BP2 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 10:
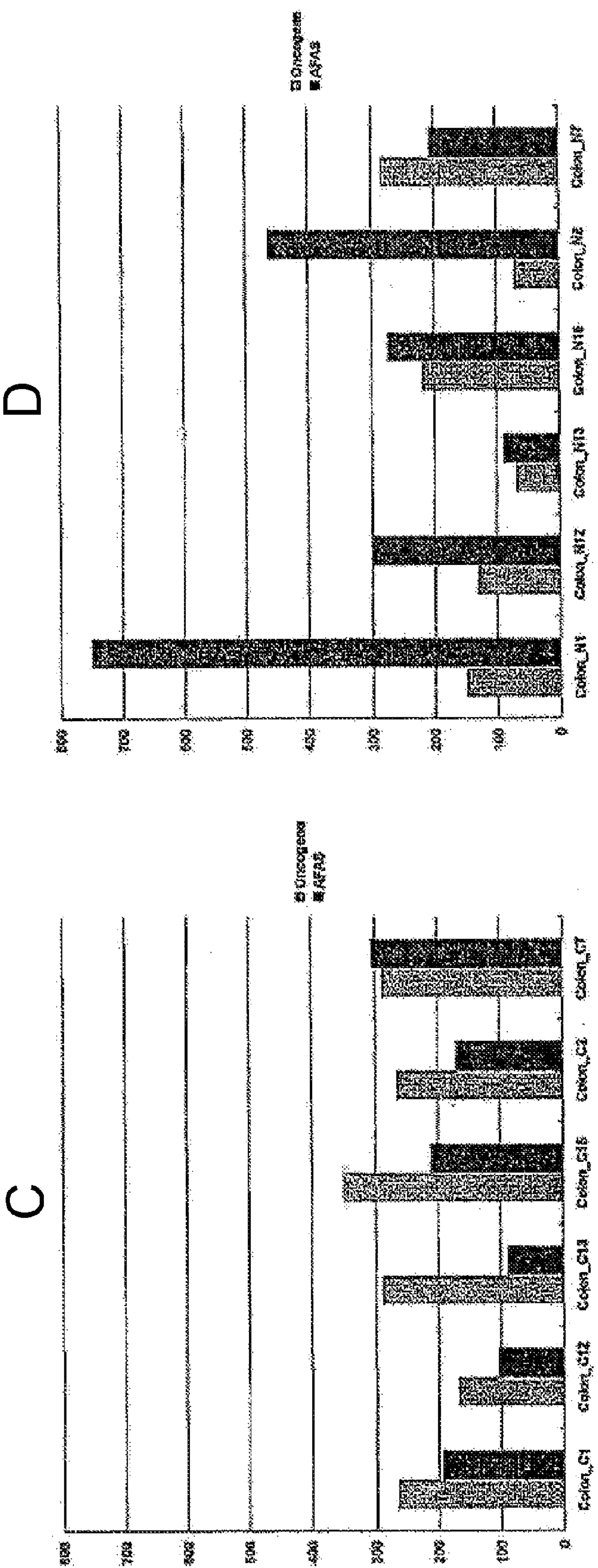
Figure 11:
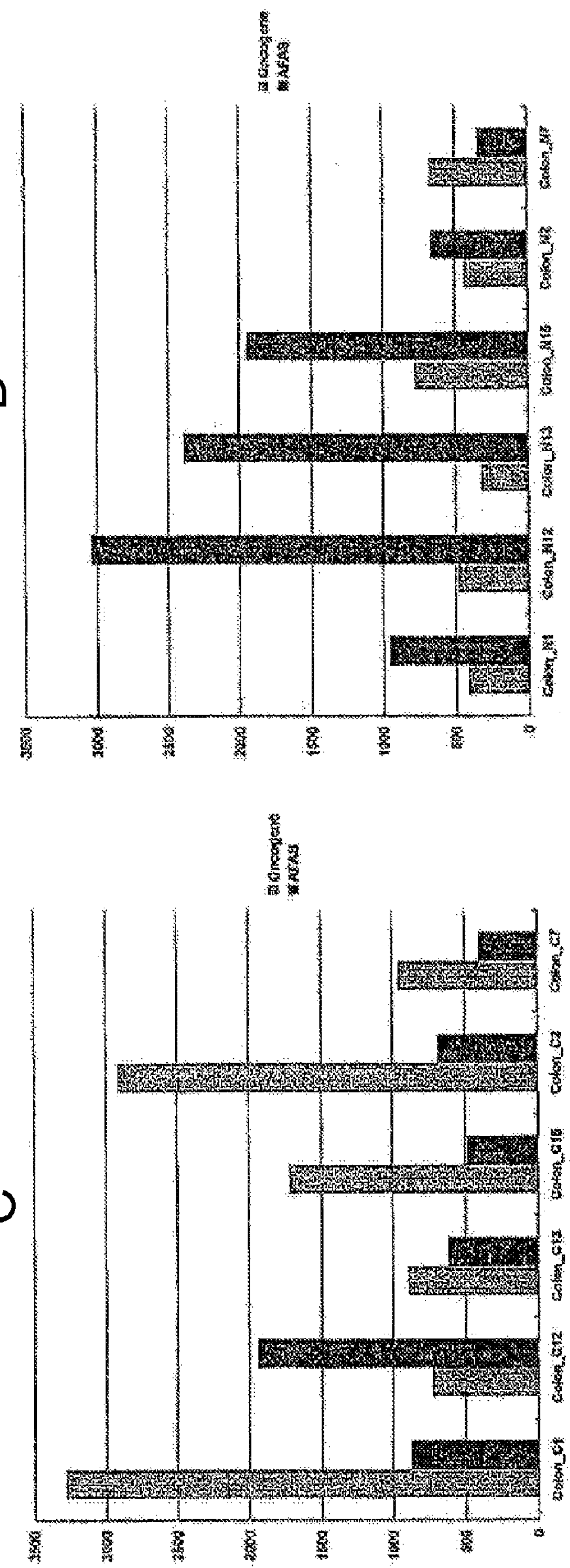
FIG. 11 shows the expression of type IV collagen α3 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 12:
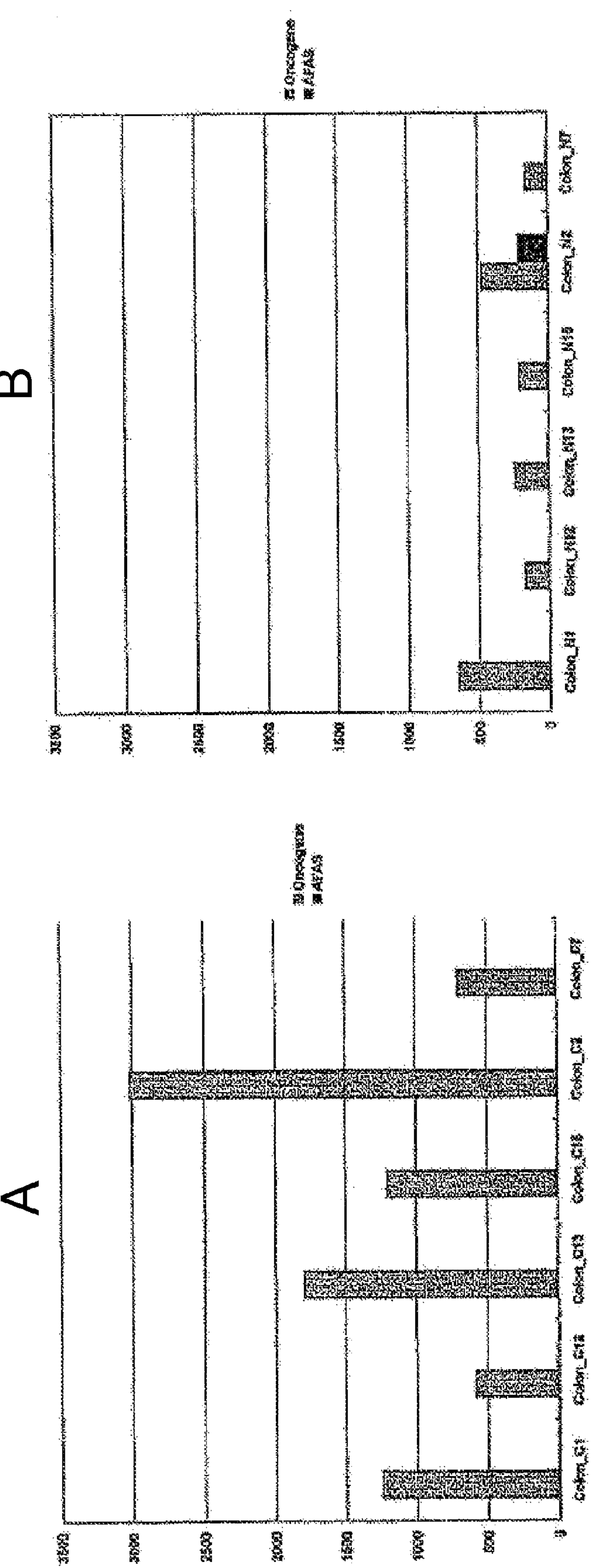
FIG. 12 shows the expression of MMP11 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 13:
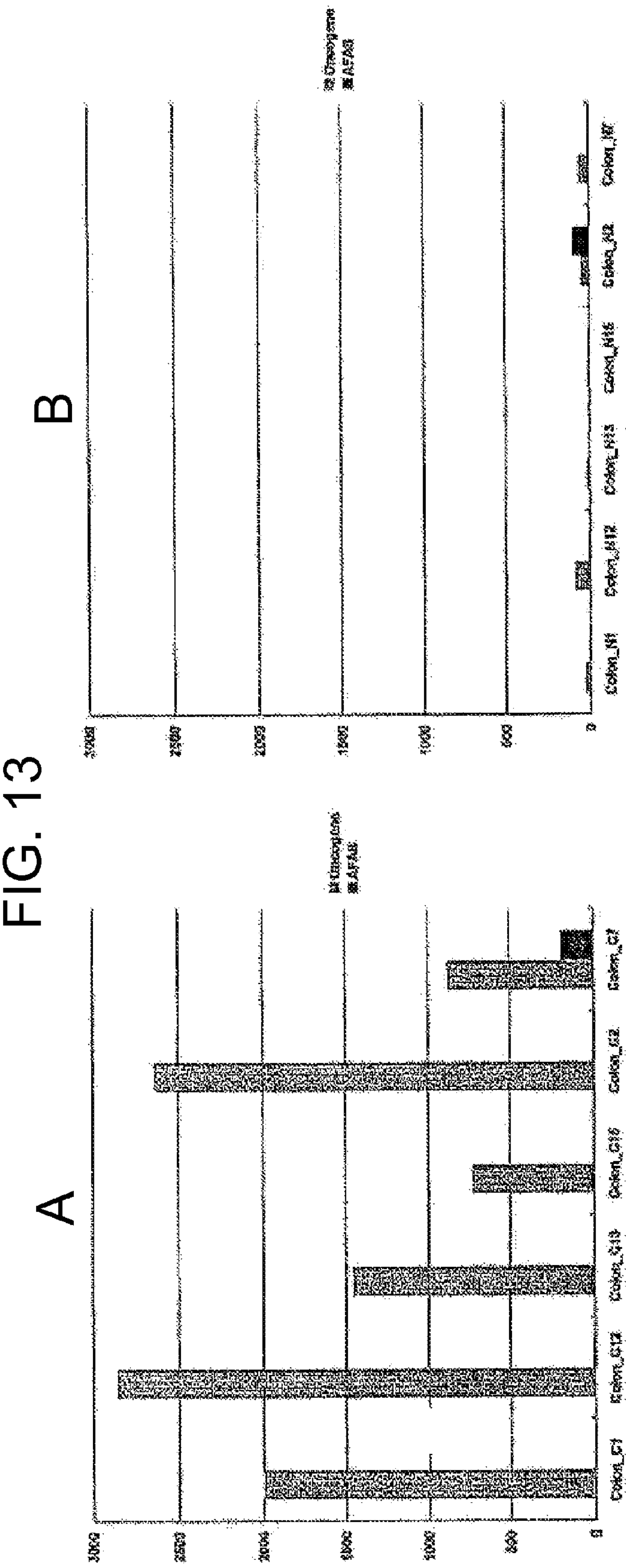
FIG. 13 shows the expression of P-cadherin in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 14:
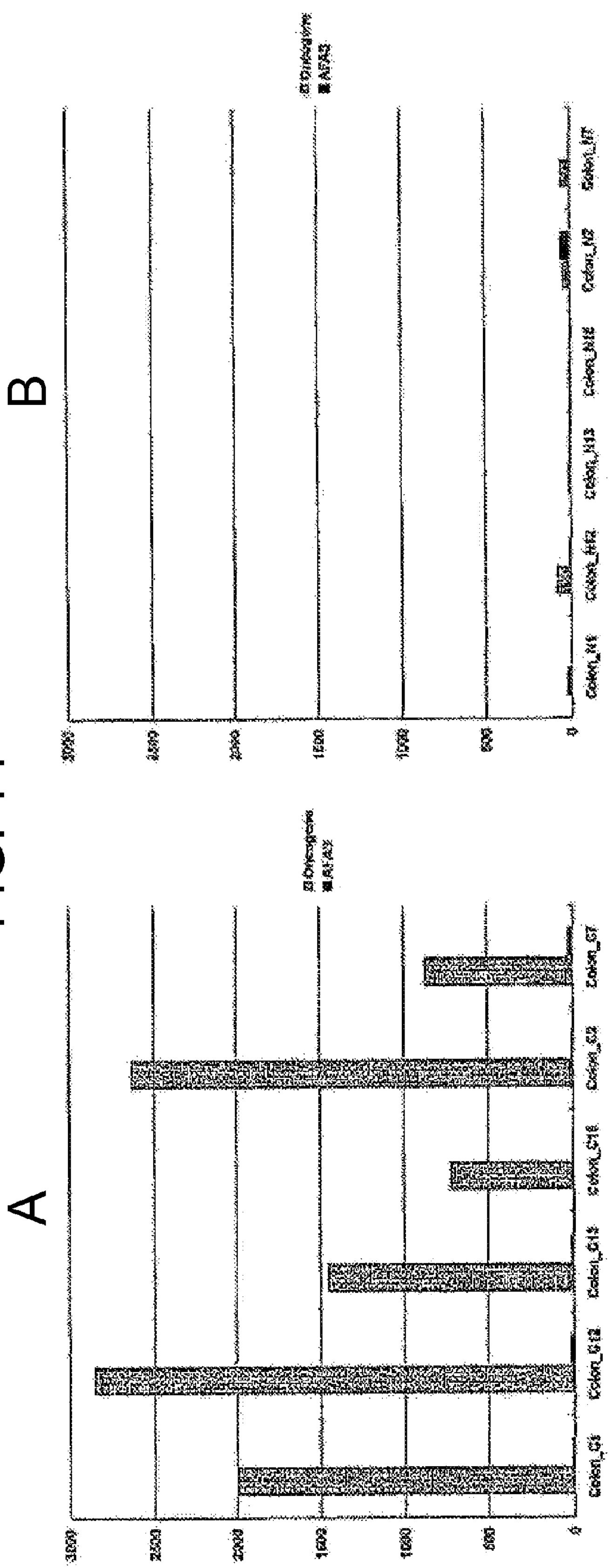
FIG. 14 shows the expression of P-cadherin in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 14:
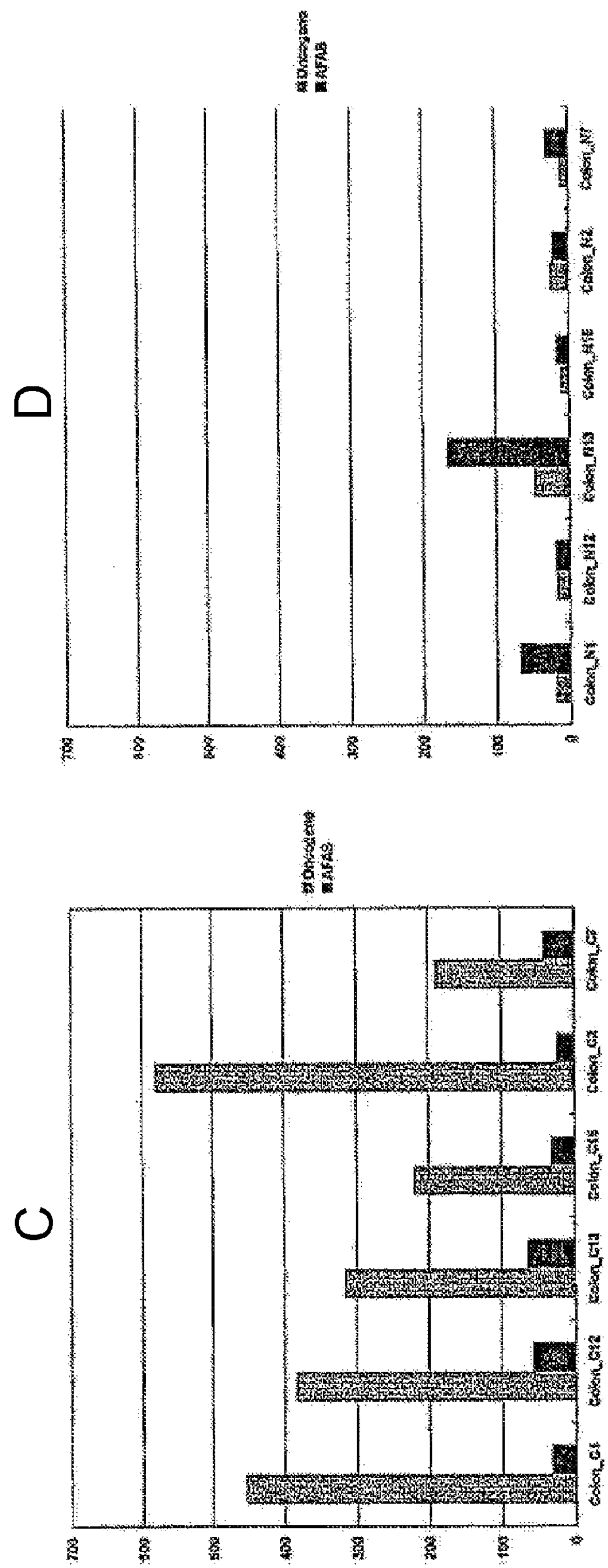
Figure 15:
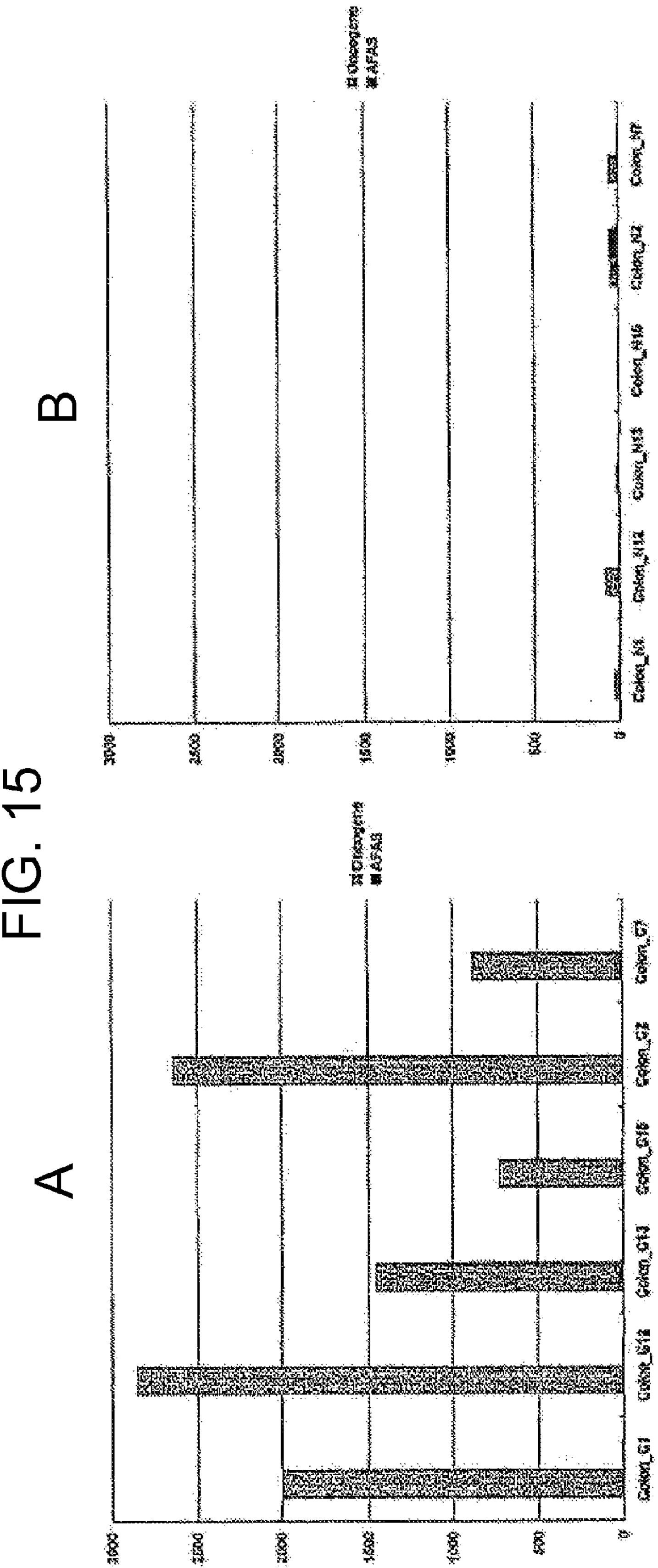
FIG. 15 shows the expression of P-cadherin in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 15:
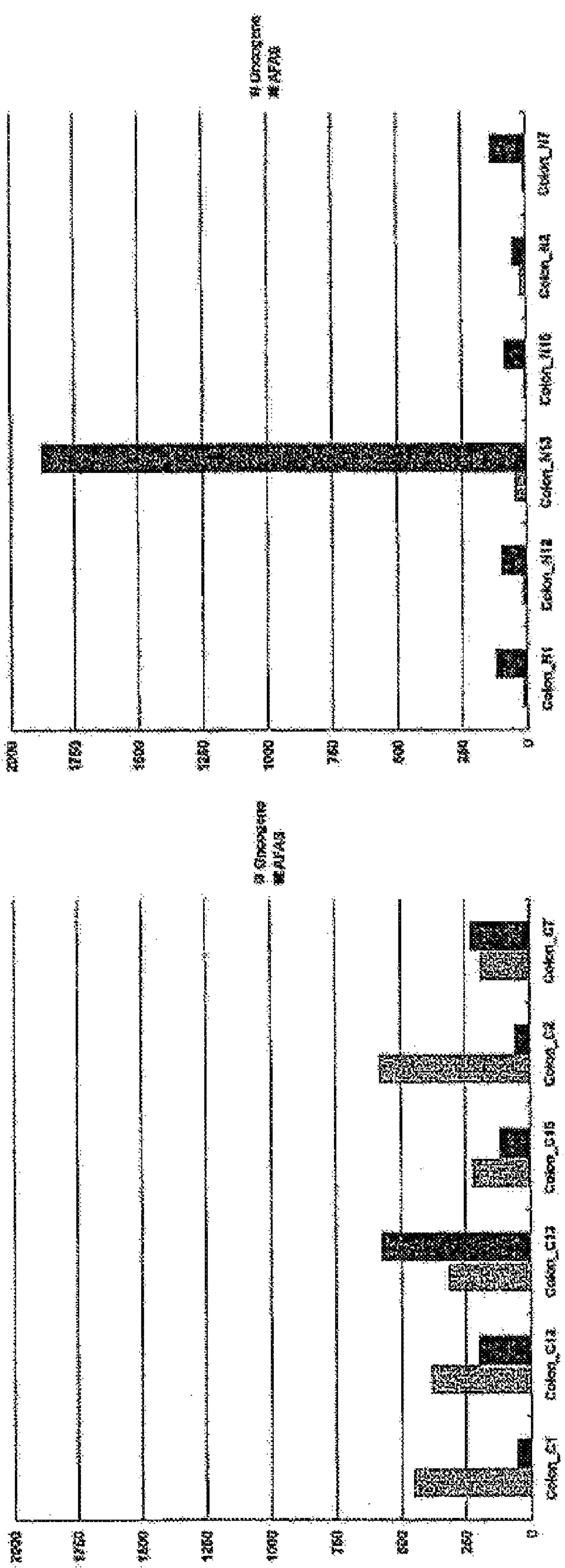

The obtained samples were labeled by the oligo(dT) priming method and analyzed. As a result, for any genes, sense RNA showed generally higher expression in colorectal cancer samples than in normal tissues, but expression of antisense RNA was not detected or detected only at low levels (A and B of FIGS. 1 to 15). On the other hand, when the samples were labeled by the random priming method, antisense RNA showed significant lower relative expression to sense RNA in colorectal cancer samples as compared to normal tissues, and the sense strand/antisense strand expression was reversed between normal and the cancer samples (C and D of FIGS. 1 to 15).

(2) Expression Analysis of Hepatic Cancer Sample

The expression of the sense strand and the antisense strand of 10 genes known to increase due to hepatic cancer was analyzed according to the above-mentioned method. The probes used were nucleotide sequences complementary to the nucleotide sequences shown by the respective sequence identification numbers listed in Table 2 in order to target the nucleotide sequences as a sense strand and antisense strand, respectively.

TABLE 2

| gene name | GenBank ID | sense strand | antisense strand |
|---|---|---|---|
| MAPK7 | U25278 | SEQ ID NO:39 | SEQ ID NO:16 |
| FGFR4 | L03840 | SEQ ID NO:40 | SEQ ID NO:17 |
| thrombospondin 2 | L12350 | SEQ ID NO:41 | SEQ ID NO:18 |
| cadherin 13 | M25753 | SEQ ID NO:29 | SEQ ID NO:3 |
| cadherin 13 | M25753 | SEQ ID NO:29 | SEQ ID NO:19 |

TABLE 2-continued

| gene name | GenBank ID | sense strand | antisense strand |
|---|---|---|---|
| cadherin 13 | M25753 | SEQ ID NO:29 | SEQ ID NO:20 |
| PCNA | M15796 | SEQ ID NO:42 | SEQ ID NO:21 |
| PDGFR | M21616 | SEQ ID NO:43 | SEQ ID NO:22 |
| cyclin B1 | M25753 | SEQ ID NO:30 | SEQ ID NO:23 |
| ERCC3 | M31899 | SEQ ID NO:44 | SEQ ID NO:24 |
| CD34 antigen | M81104 | SEQ ID NO:45 | SEQ ID NO:25 |
| integrin α6 | X53586 | SEQ ID NO:46 | SEQ ID NO:26 |

As the analysis samples, the samples of five hepatic cancer patients were used and, in the same manner as in the above-mentioned (1), RNA was extracted from cancer tissue and the surrounding normal tissues.

Figure 16:
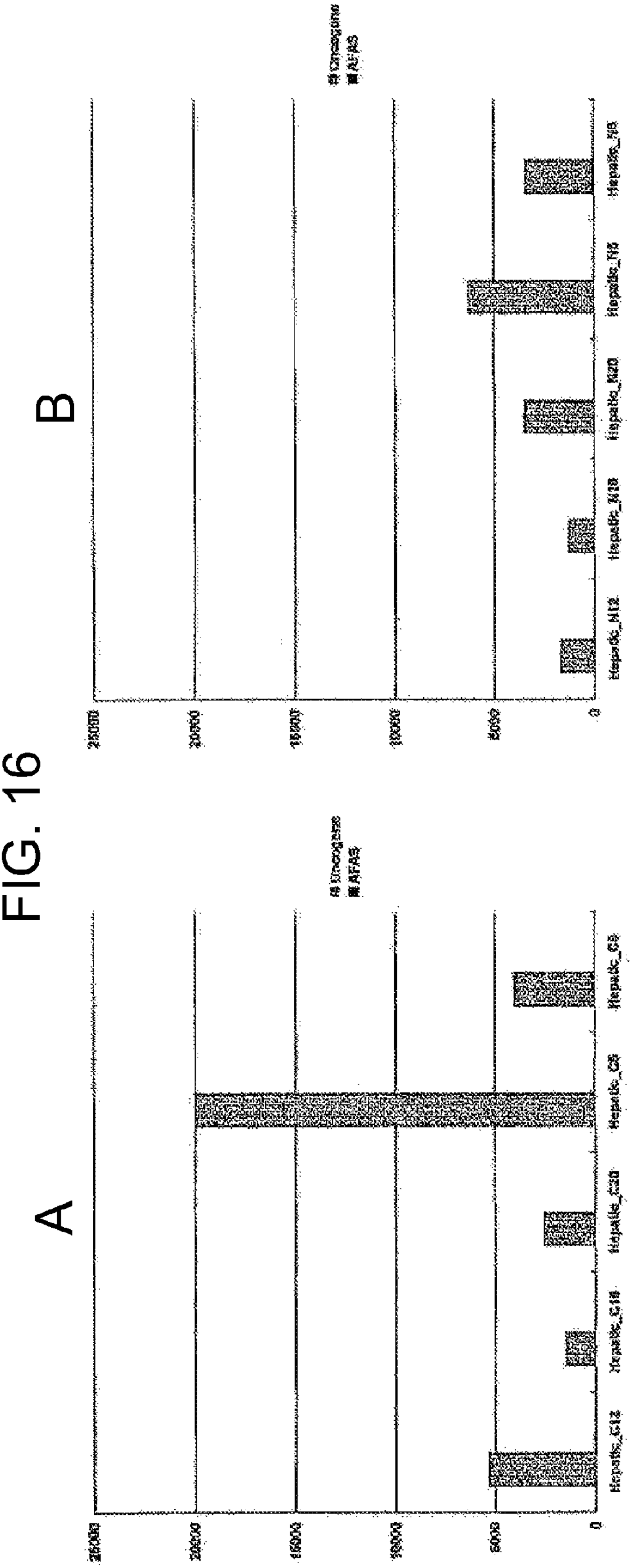
FIG. 16 shows the expression of MAPK7 in hepatic cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 16:
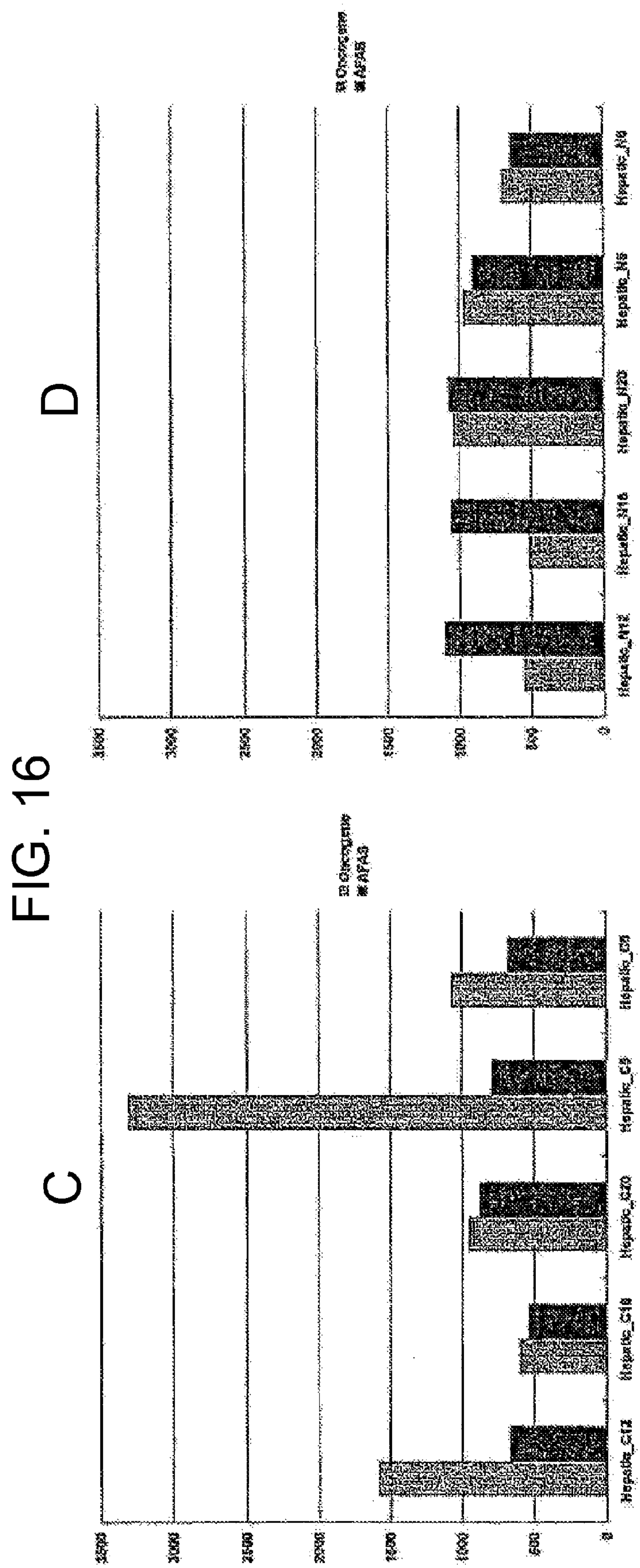
Figure 18:
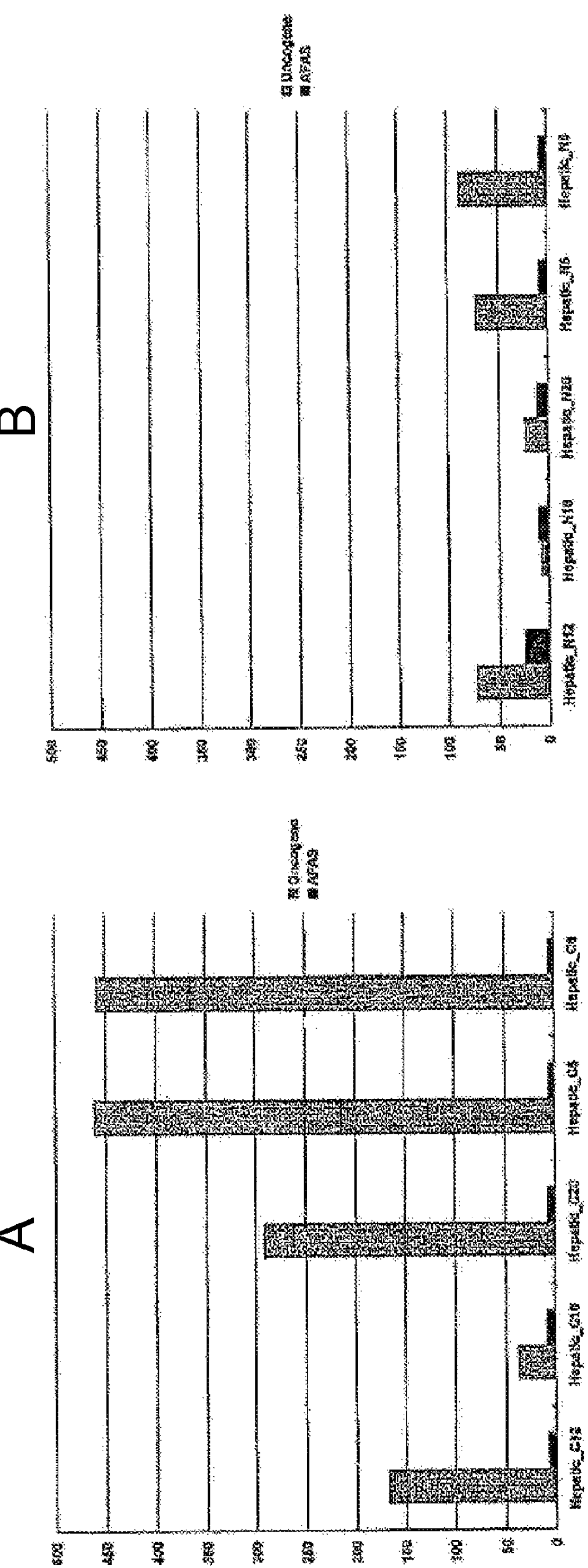
FIG. 18 shows the expression of thrombospondin 2 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 18:
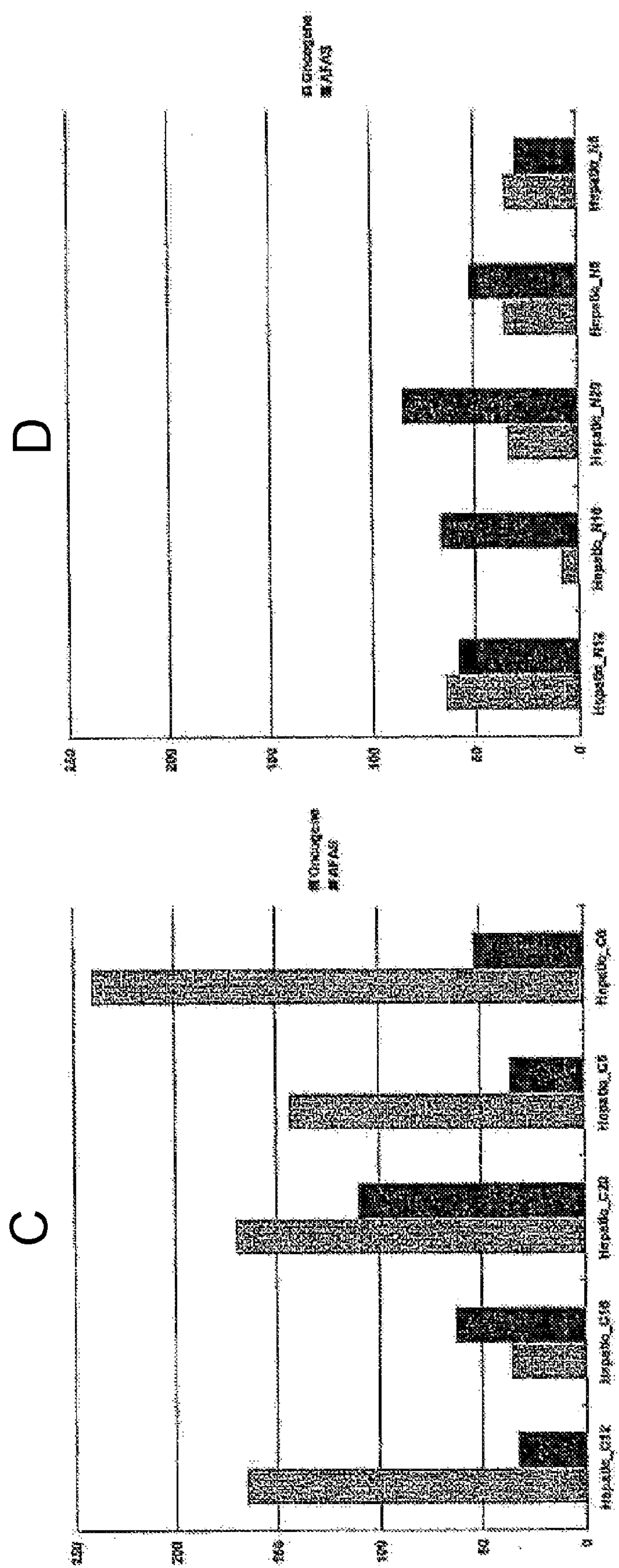
Figure 19:
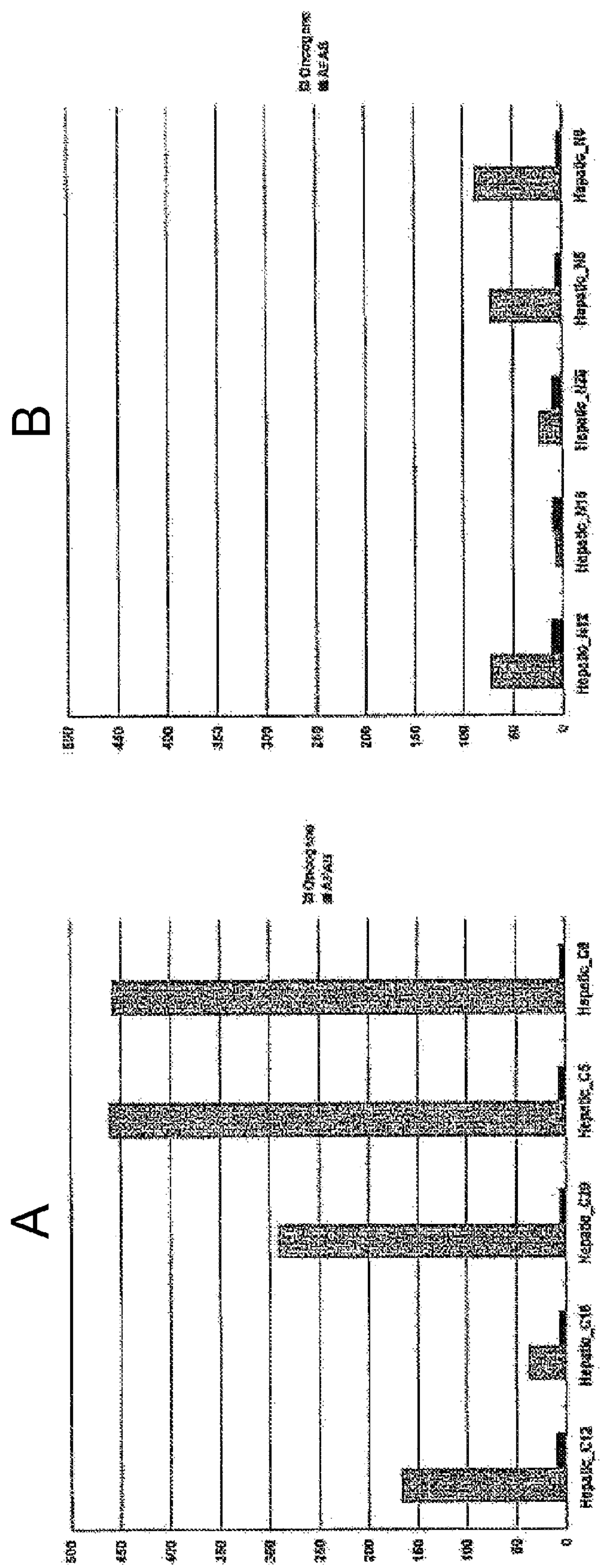
FIG. 19 shows the expression of cadherin 13 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 19:
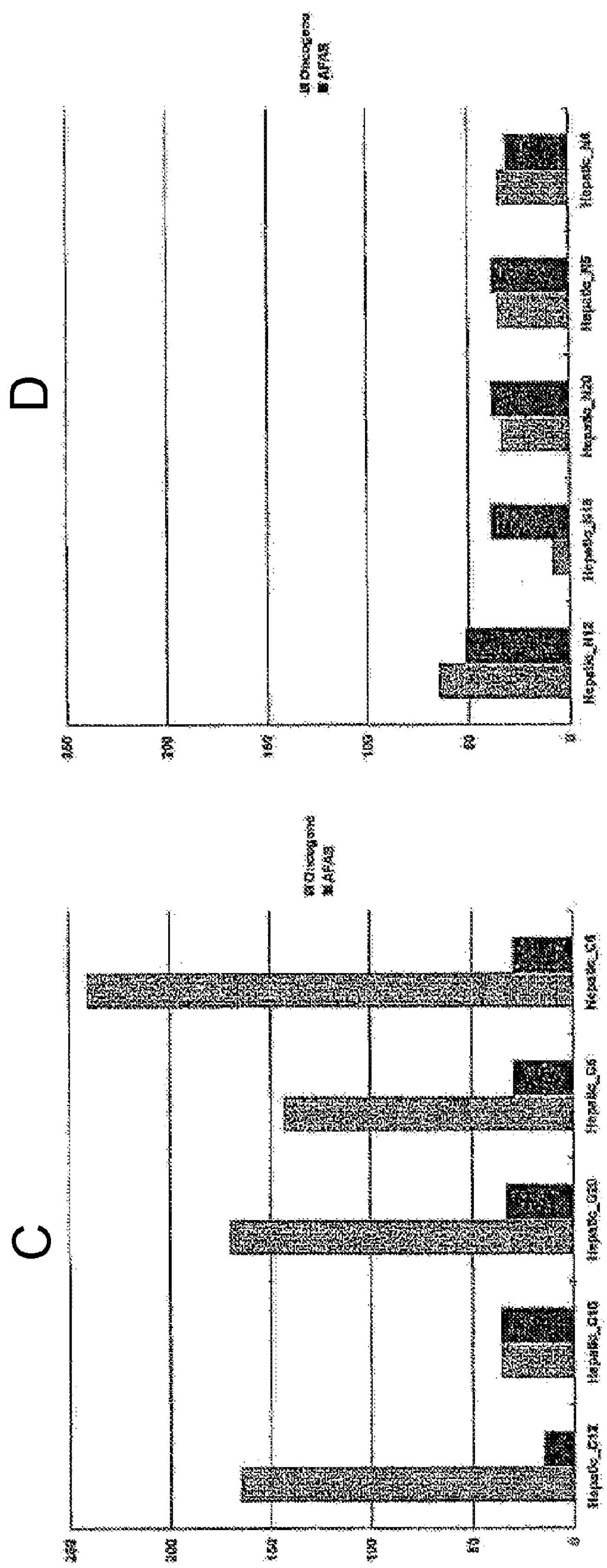
Figure 20:
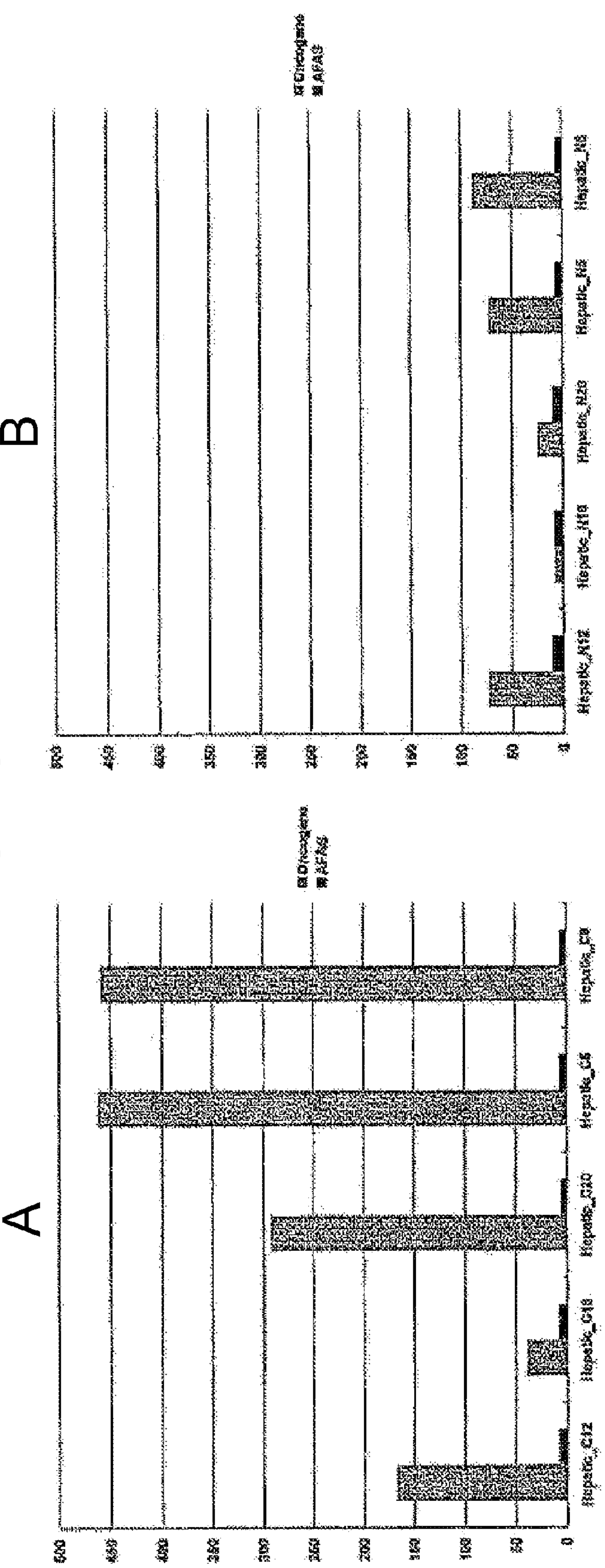
FIG. 20 shows the expression of cadherin 13 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 21:
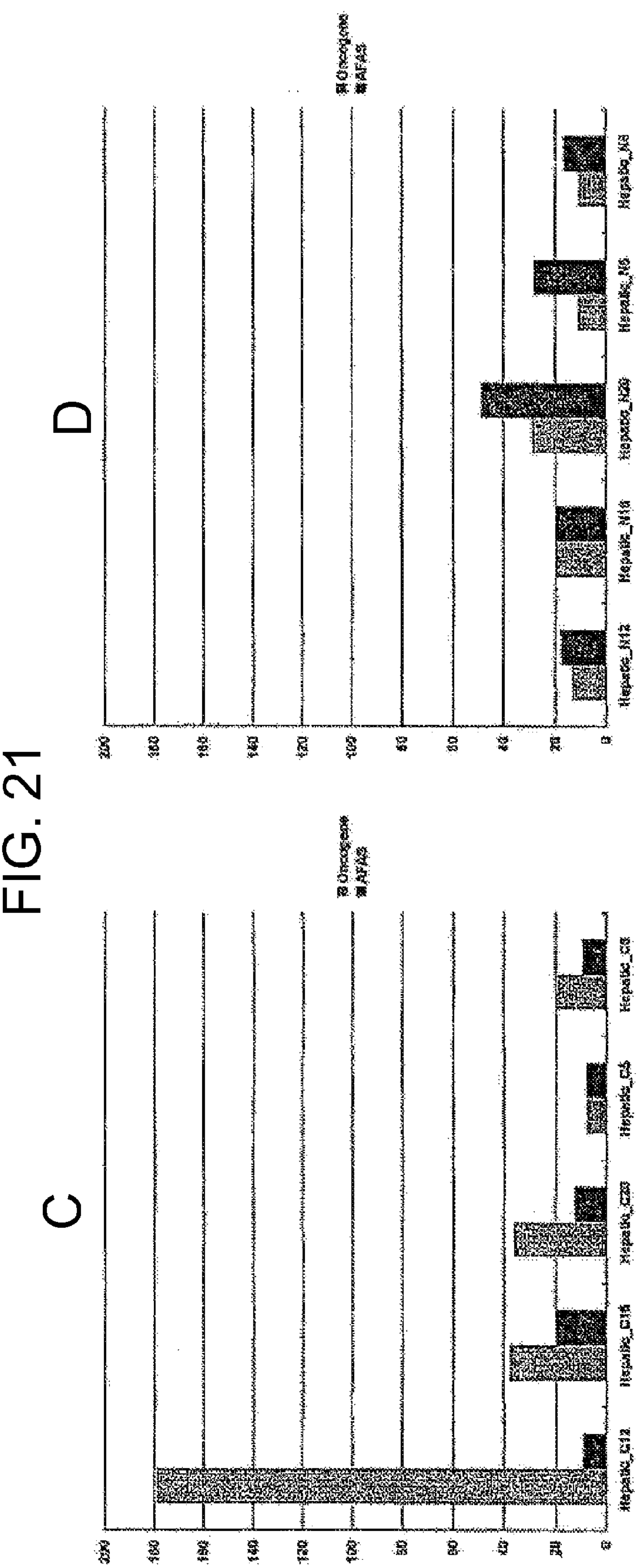
FIG. 21 shows the expression of cadherin 13 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 22:
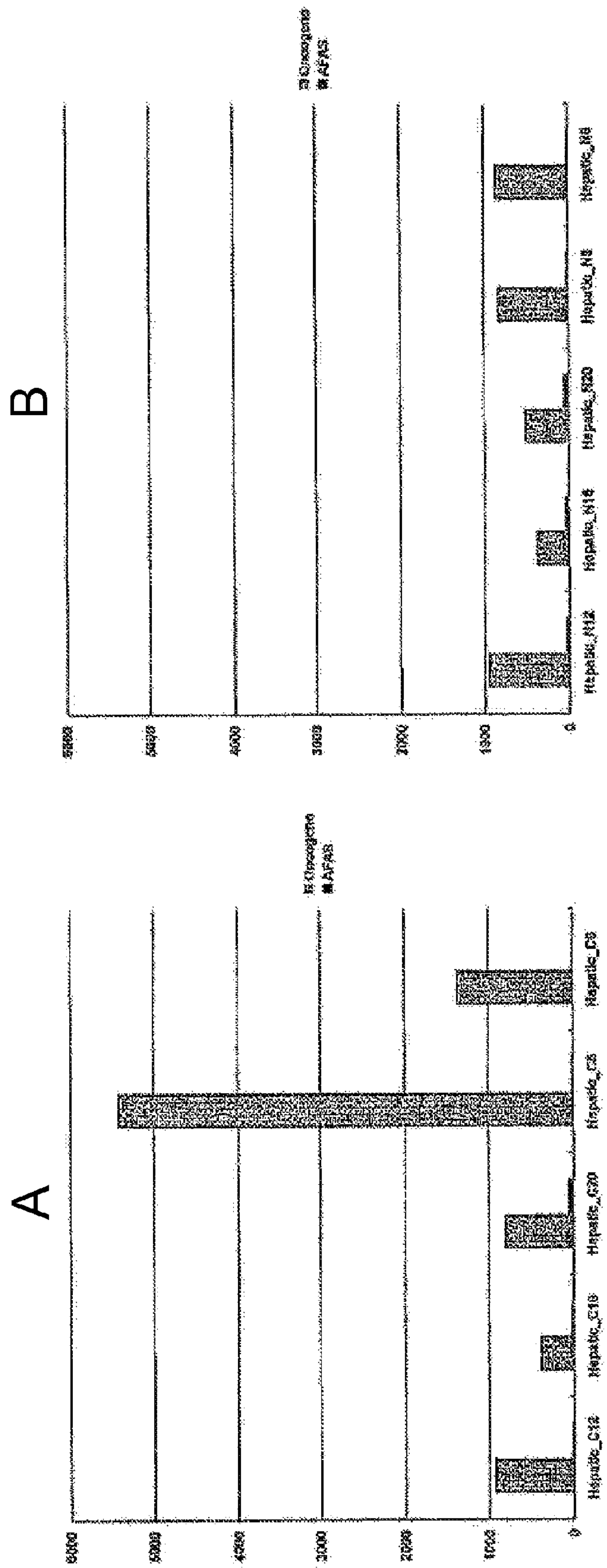
FIG. 22 shows the expression of PCNA in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 22:
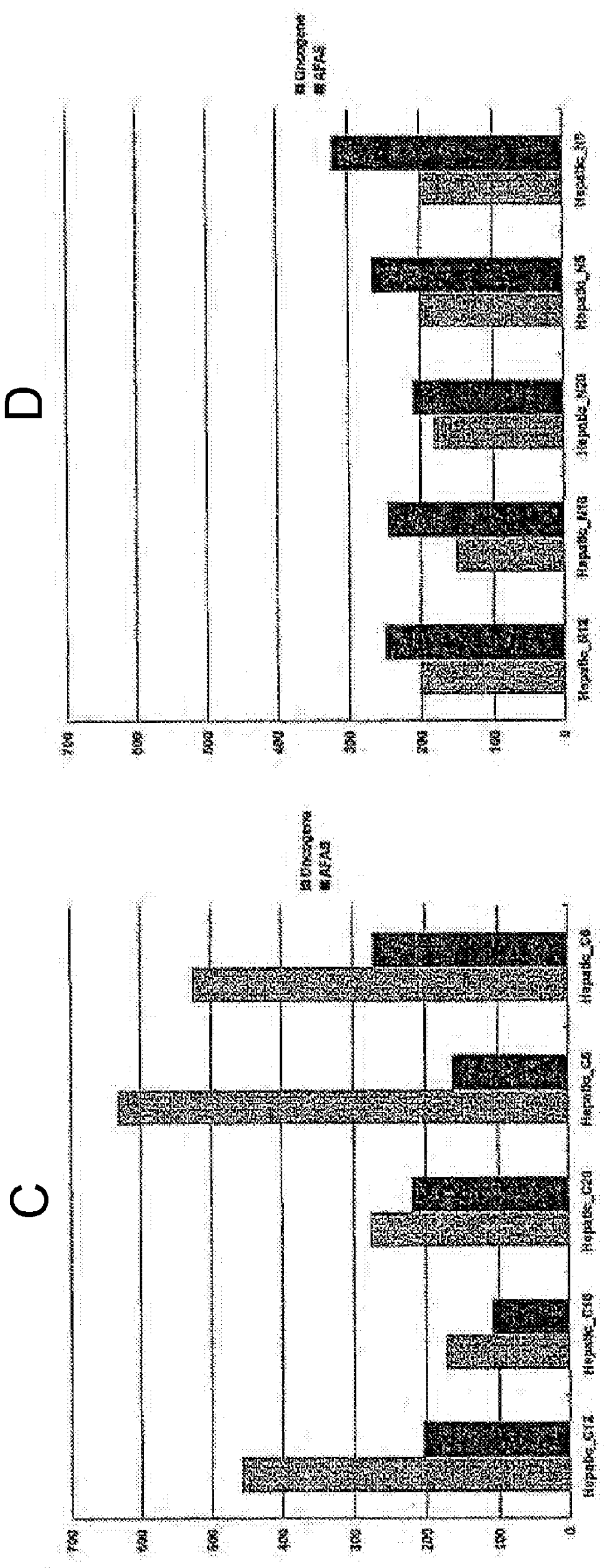
Figure 23:
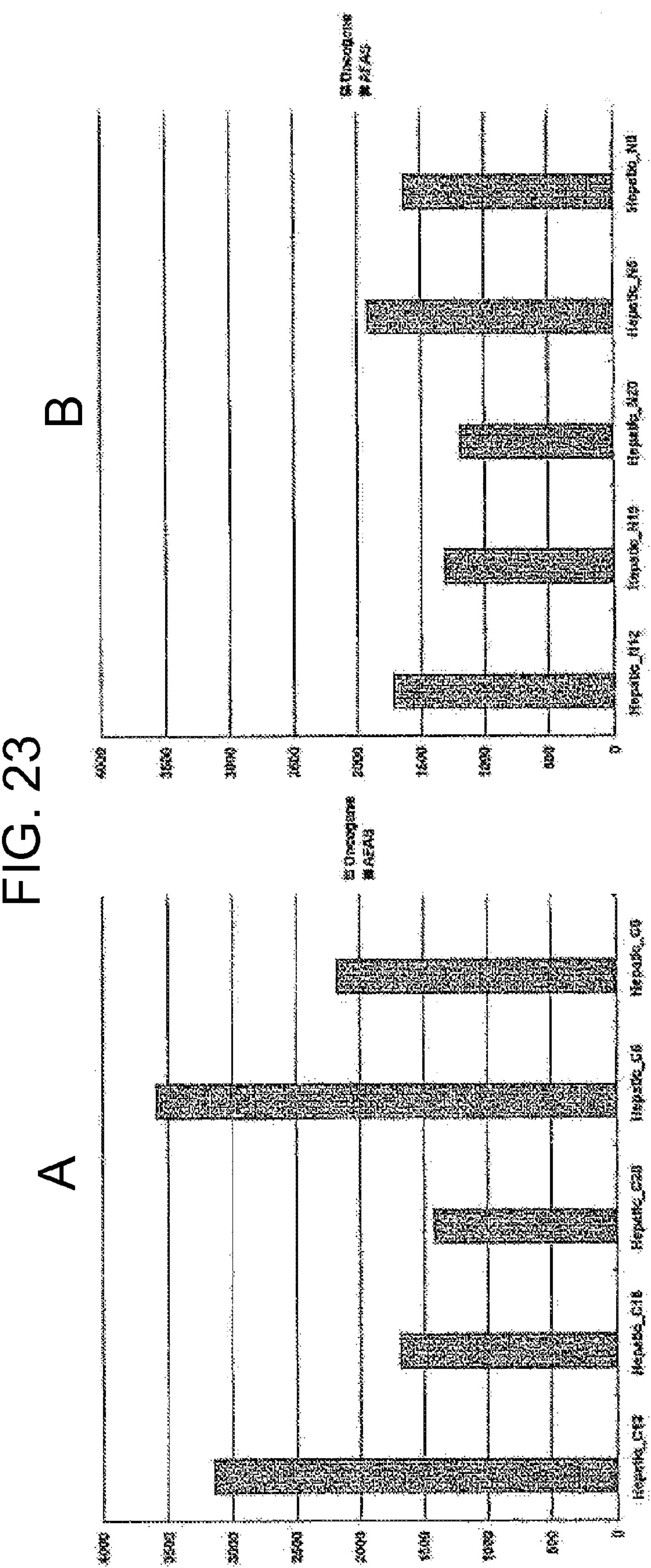
FIG. 23 shows the expression of PDGFR in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 23:
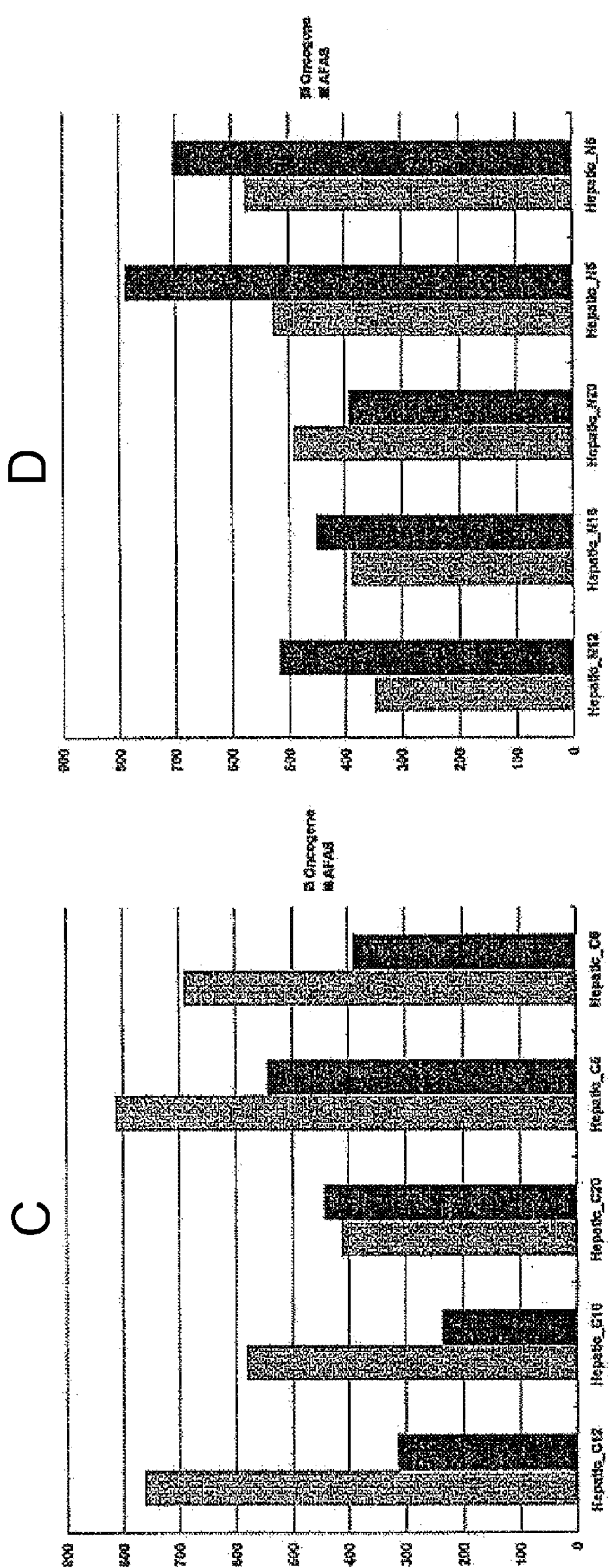
Figure 24:
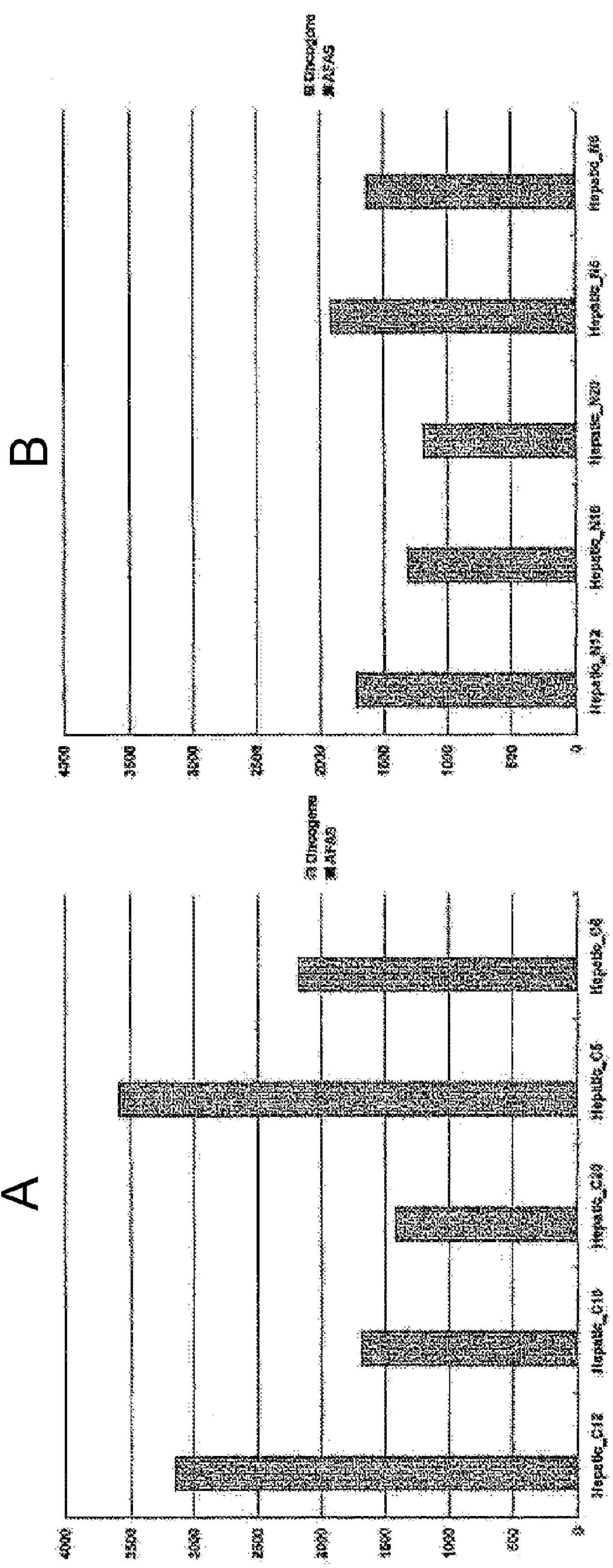
FIG. 24 shows the expression of cyclin B1 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 24:
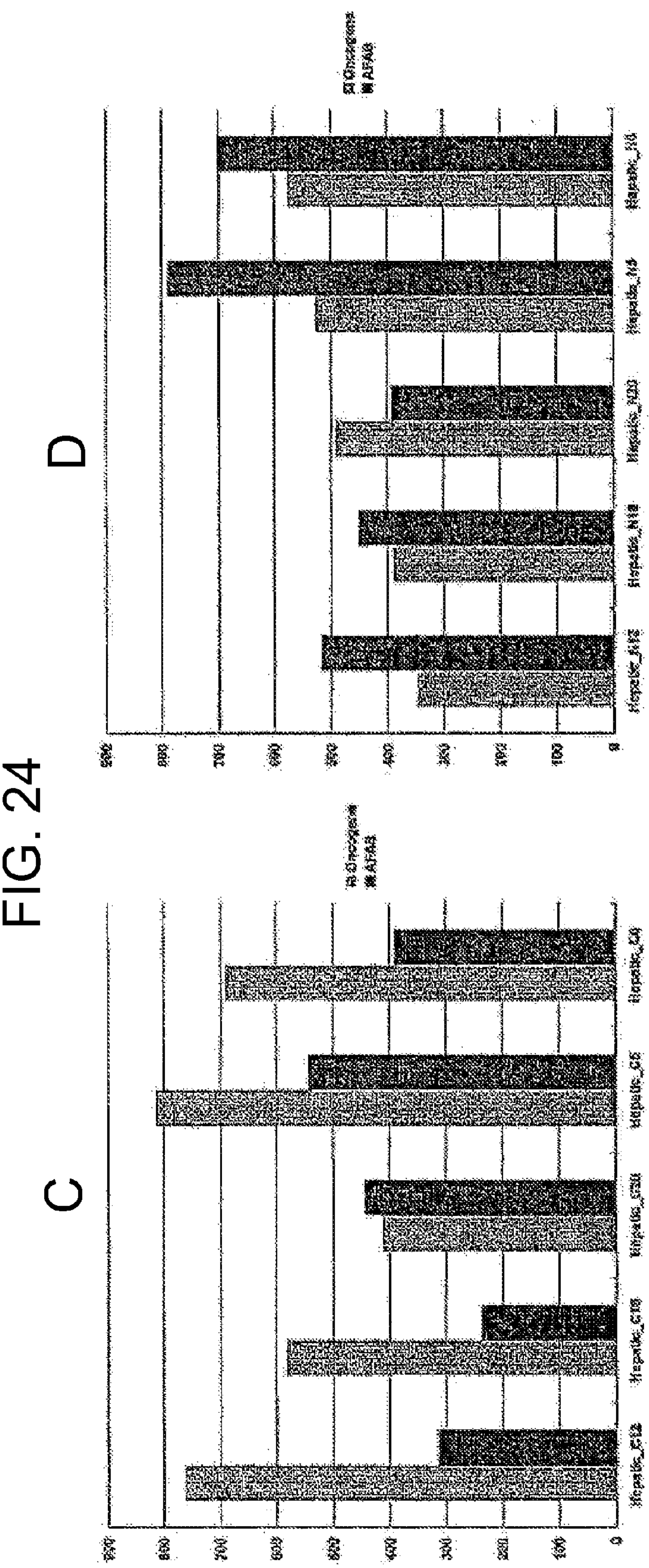
Figure 25:
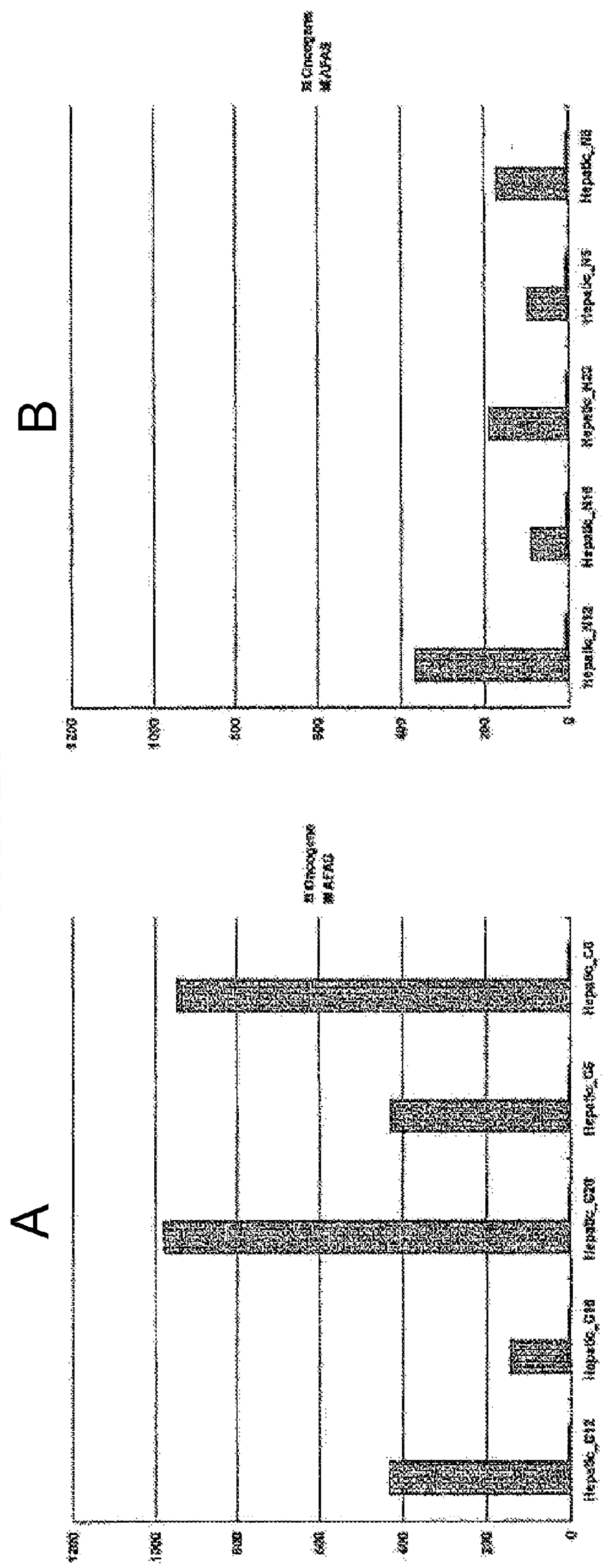
FIG. 25 shows the expression of ERCC3 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 25:
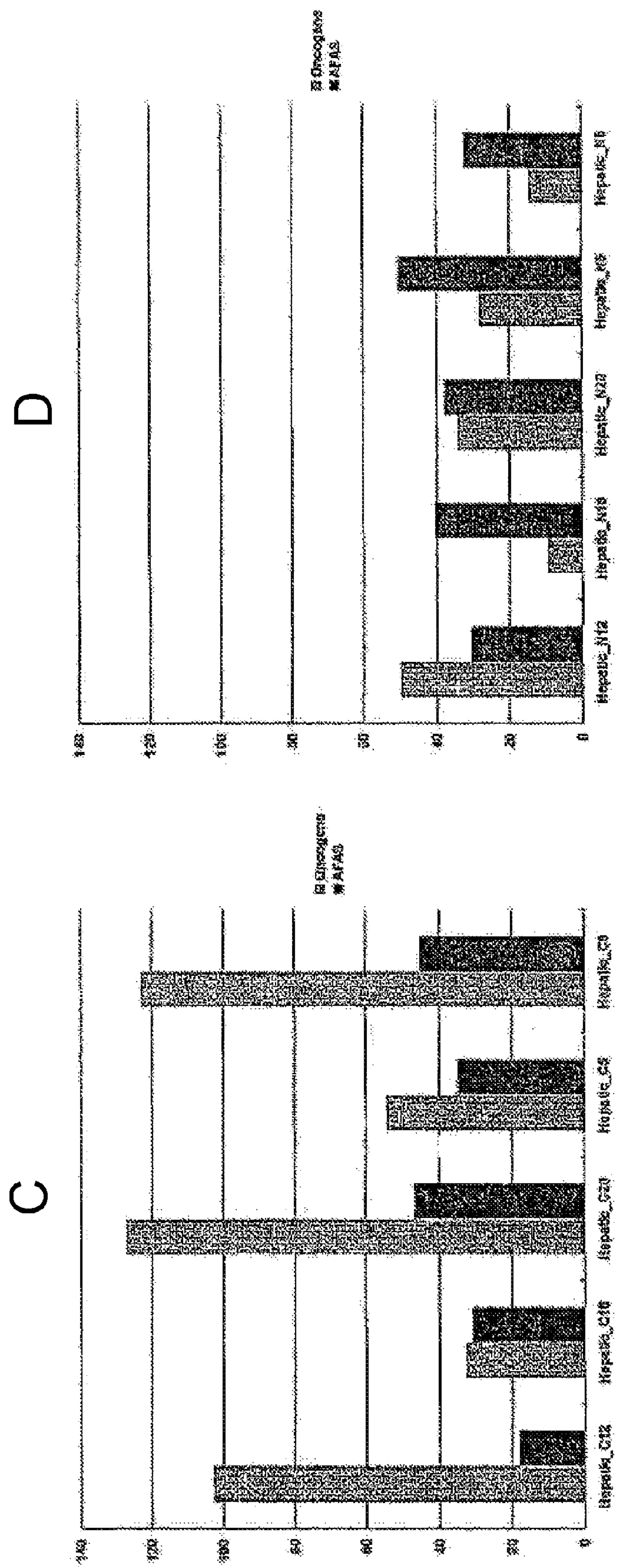
Figure 26:
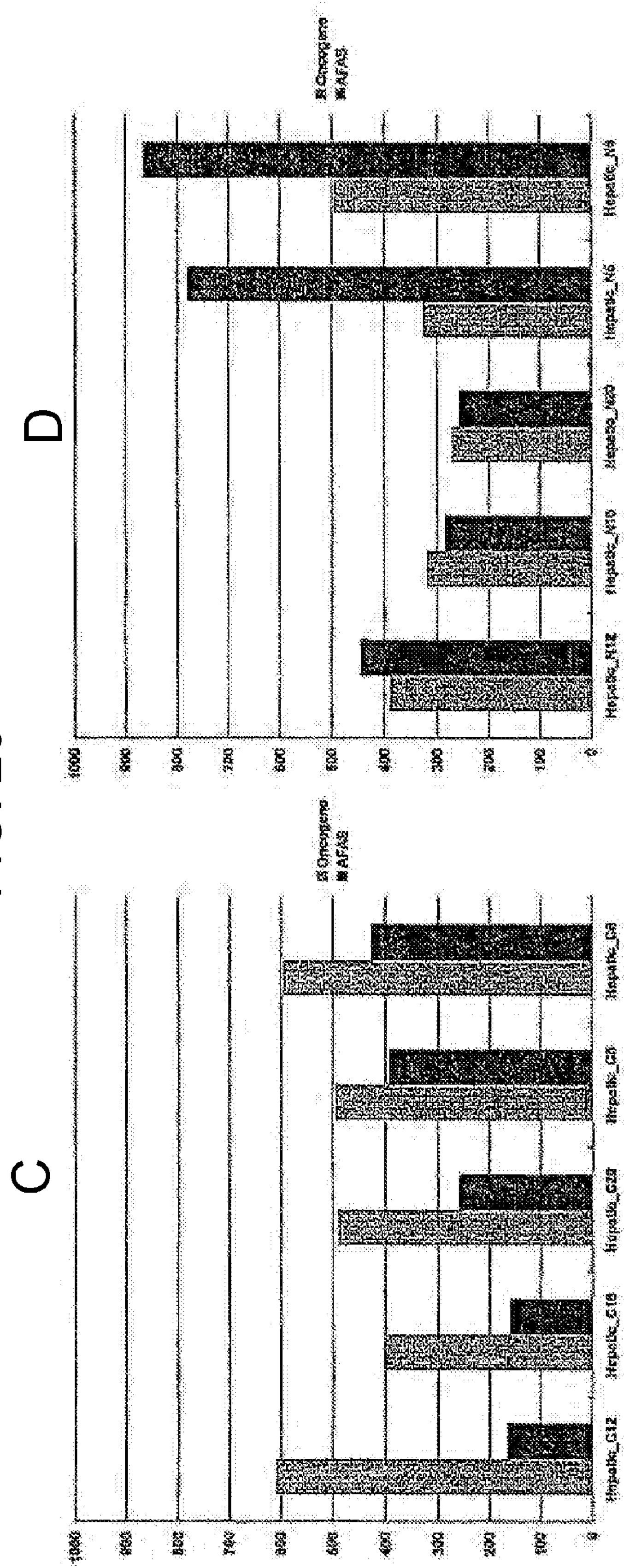
FIG. 26 shows the expression of CD34 antigen in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 27:
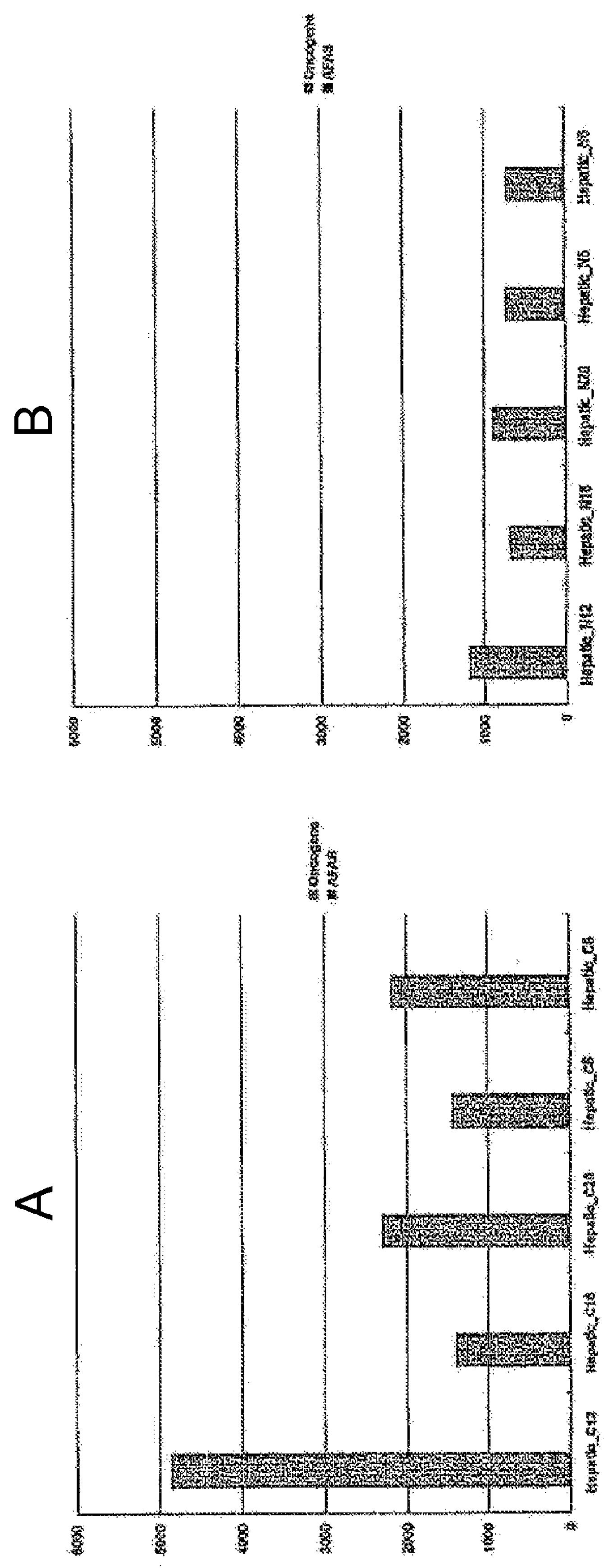
FIG. 27 shows the expression of integrin α6 in colorectal cancer tissue samples (A and C) and normal tissue samples (B and D) determined by the oligo-dT priming (A and B) or the random priming (C and D). The six columns on the axis of abscissas are individual patients; the left bar for each column indicates the expression of a sense strand, and the right bar indicates the expression of an antisense strand.
Figure 27:
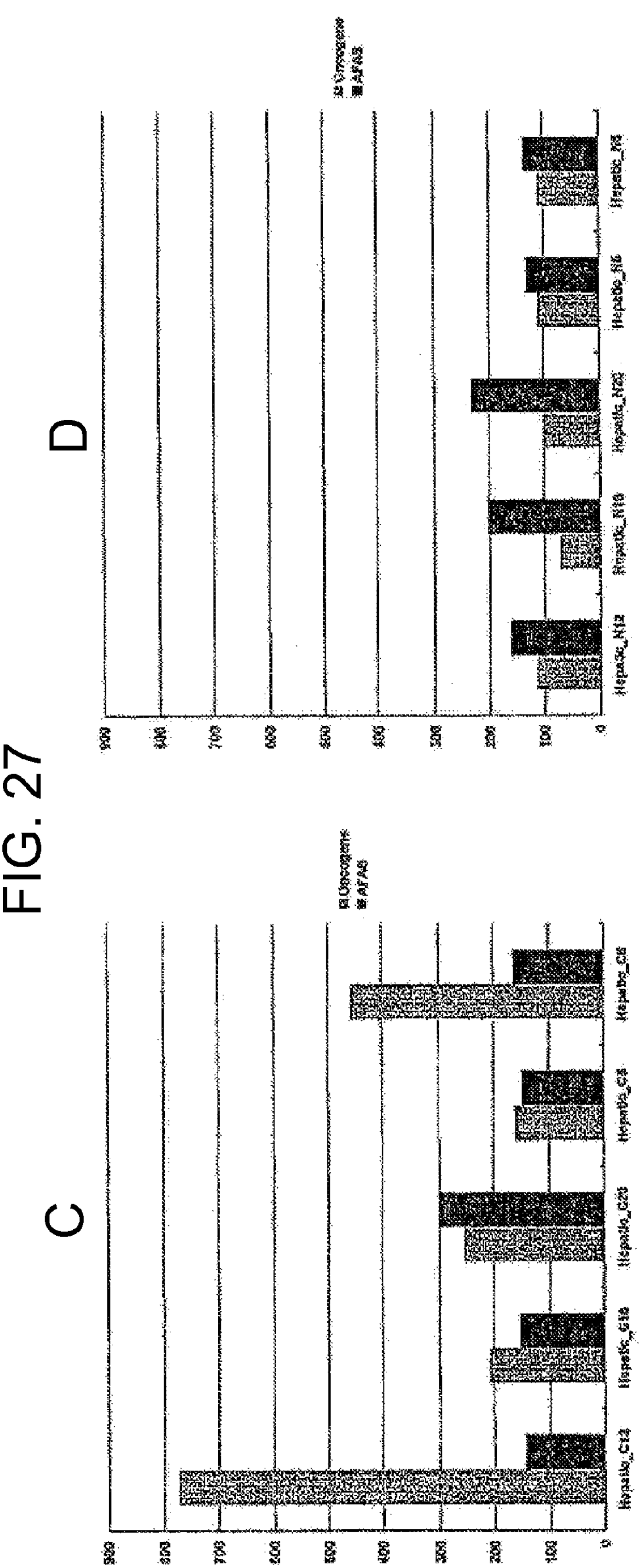

Similar to the colorectal cancer samples, the samples were labeled by the oligo(dT) priming method and analyzed. As a result, sense RNA showed generally higher expression in hepatic cancer samples than in normal tissues (A and B of FIGS. 16 to 27). On the other hand, when the samples were labeled by the random priming method, antisense RNA showed significantly lower relative expression to sense RNA in hepatic cancer samples as compared to normal tissues, and the sense strand/antisense strand expression was reversed between normal and the cancer samples (C and D of FIGS. 16 to 27).

The above results indicate that colorectal cancer and hepatic cancer patients show specific expression patterns in that the expression of sense strand and antisense strand of the genes recited in Tables 1 and 2 are reversed between normal tissue and cancer sample. It is strongly suggested therefrom that sense strand RNA and antisense strand RNA control expression of each other by an interaction through formation of double stranded RNA and the like.

Industrial Applicability

The novel endogenous antisense RNAs according to the present invention are useful as cancer markers because they exhibit remarkably decreased expression in cancer patients compared with healthy persons. These endogenous antisense RNAs can also be useful in designing more effective and safer antisense pharmaceuticals or RNAi pharmaceuticals because they are thought to suppresses the translation of mRNAs from sense strands into proteins by the same action mechanisms as those of antisense pharmaceuticals or RNAi pharmaceuticals.

This application is based on a patent application No. 2007-146342 filed in Japan, the contents of which are incorporated in full herein by this reference.

What is claimed is:

1. A method for cancer diagnosis comprising measuring an endogenous antisense RNA that lacks a poly(A) chain in an RNA-containing sample collected from a mammal by labeling the RNA-containing sample by random priming and using a microarray containing a probe for the endogenous poly(A)-less antisense RNA, wherein the endogenous antisense RNA that lacks a poly(A) chain is an endogenous antisense RNA of mammalian P-cadherin gene comprising the nucleotide sequence of SEQ ID NO:13, and wherein decreased expression of the antisense RNA relative to the expression of the corresponding sense RNA is indicative of cancer cells as compared to normal cells.

2. The method of claim 1, further comprising measuring the sense RNA.

3. The method of claim 1, wherein the microarray further contains a probe for the corresponding sense RNA.

4. The method of claim 3, wherein the endogenous poly (A)-less antisense RNA is present in nucleus.

* * * * *